(12) United States Patent
Freeman et al.

(10) Patent No.: US 11,009,870 B2
(45) Date of Patent: May 18, 2021

(54) VEHICLE COMPATIBLE AMBULATORY DEFIBRILLATOR

(71) Applicant: ZOLL Medical Corporation, Chelmsford, MA (US)

(72) Inventors: Gary A Freeman, Waltham, MA (US); Guy R Johnson, Wilton, NH (US); Gregory R Frank, Mt. Lebanon, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 212 days.

(21) Appl. No.: 16/000,211

(22) Filed: Jun. 5, 2018

(65) Prior Publication Data
US 2018/0348759 A1    Dec. 6, 2018

Related U.S. Application Data

(60) Provisional application No. 62/515,563, filed on Jun. 6, 2017.

(51) Int. Cl.
*G05B 1/00* (2006.01)
*A61B 5/00* (2006.01)
(Continued)

(52) U.S. Cl.
CPC .......... *G05D 1/0061* (2013.01); *A61B 5/021* (2013.01); *A61B 5/024* (2013.01); *A61B 5/6893* (2013.01);
(Continued)

(58) Field of Classification Search
CPC .... A61N 1/3904; A61N 1/046; A61N 1/3937; A61B 5/747; A61B 5/024; A61B 5/021;
(Continued)

(56) References Cited

U.S. PATENT DOCUMENTS

| 4,094,310 A | 6/1978 | McEachern et al. |
| 4,432,368 A | 2/1984 | Russek |

(Continued)

FOREIGN PATENT DOCUMENTS

| CN | 101031334 A | 9/2007 |
| CN | 101657229 A | 2/2010 |

(Continued)

OTHER PUBLICATIONS

Chueng, Michael, M.H. et al., Randomized Controlled Trial of the Effects of Remote Ischemic Preconditioning on Children Undergoing Cardiac Surgery, Journal of the American College of Cardiology, vol. 47, No. 11, Jun. 6, 2006, pp. 2277-2282.

(Continued)

*Primary Examiner* — Mussa A Shaawat
(74) *Attorney, Agent, or Firm* — ZOLL Medical Corporation

(57) ABSTRACT

An ambulatory medical device that can communicate with a vehicle is described. An example of the ambulatory medical device includes one or more sensing electrodes configured to sense cardiopulmonary signals of a patient, a network interface, and one or more processors configured to receive signals from one or more vehicle occupancy sensors, detect usage of the ambulatory medical device in a vehicle based on the received signals from the one or more vehicle occupancy sensors, detect at least one of a medical event and a medical premonitory event of the patient based on the sensed cardiopulmonary signals, and provide driving control information to the vehicle, via the network interface, based at least in part on the detected usage of the ambulatory medical device in the vehicle and the detected medical event or medical premonitory event of the patient.

27 Claims, 8 Drawing Sheets

(51) Int. Cl.

| | | |
|---|---|---|
| *A61B 5/021* | (2006.01) | |
| *A61B 5/024* | (2006.01) | |
| *A61N 1/04* | (2006.01) | |
| *A61N 1/39* | (2006.01) | |
| *B60Q 9/00* | (2006.01) | |
| *G01C 21/34* | (2006.01) | |
| *G16H 10/60* | (2018.01) | |
| *G05D 1/00* | (2006.01) | |
| *G16H 50/20* | (2018.01) | |
| *G16H 50/30* | (2018.01) | |

(52) U.S. Cl.
CPC ............ *A61B 5/747* (2013.01); *A61N 1/3904* (2017.08); *B60Q 9/00* (2013.01); *G01C 21/3415* (2013.01); *G05D 1/0088* (2013.01); *A61N 1/046* (2013.01); *A61N 1/3937* (2013.01); *G16H 10/60* (2018.01); *G16H 50/20* (2018.01); *G16H 50/30* (2018.01)

(58) Field of Classification Search
CPC ........ G16H 50/20; G16H 50/30; G16H 10/60; G01C 21/3415
See application file for complete search history.

(56) References Cited

U.S. PATENT DOCUMENTS

| | | |
|---|---|---|
| 4,632,122 A | 12/1986 | Johansson et al. |
| 4,698,848 A | 10/1987 | Buckley |
| 4,928,690 A | 5/1990 | Heilman et al. |
| 4,978,926 A | 12/1990 | Zerod et al. |
| 5,062,834 A | 11/1991 | Gross et al. |
| 5,078,134 A | 1/1992 | Heilman et al. |
| 5,176,380 A | 1/1993 | Evans et al. |
| 5,330,505 A | 7/1994 | Cohen |
| 5,348,008 A | 9/1994 | Bornn et al. |
| 5,353,793 A | 10/1994 | Bornn |
| 5,357,696 A | 10/1994 | Gray et al. |
| 5,365,932 A | 11/1994 | Greenhut |
| 5,437,285 A | 8/1995 | Verrier et al. |
| 5,564,429 A | 10/1996 | Bornn et al. |
| 5,662,689 A | 9/1997 | Elsberry et al. |
| 5,687,738 A | 11/1997 | Shapiro et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,929,601 A | 7/1999 | Kaib et al. |
| 5,944,669 A | 8/1999 | Kaib |
| 6,016,445 A | 1/2000 | Baura |
| 6,045,503 A | 4/2000 | Grabner et al. |
| 6,065,154 A | 5/2000 | Hulings et al. |
| 6,097,982 A | 8/2000 | Glegyak et al. |
| 6,097,987 A | 8/2000 | Milani |
| 6,148,233 A | 11/2000 | Owen et al. |
| 6,169,387 B1 | 1/2001 | Kaib |
| 6,169,397 B1 | 1/2001 | Steinbach et al. |
| 6,199,904 B1 | 3/2001 | Dosdall |
| 6,253,099 B1 | 6/2001 | Oskin et al. |
| 6,280,461 B1 | 8/2001 | Glegyak et al. |
| 6,390,996 B1 | 5/2002 | Halperin et al. |
| 6,406,426 B1 | 6/2002 | Reuss et al. |
| 6,445,988 B1 | 9/2002 | Breed et al. |
| 6,506,153 B1 | 1/2003 | Littek et al. |
| 6,603,999 B2 | 8/2003 | SerVaas |
| 6,609,023 B1 | 8/2003 | Fischell et al. |
| 6,666,830 B1 | 12/2003 | Lehrman et al. |
| 6,681,003 B2 | 1/2004 | Linder et al. |
| 6,690,969 B2 | 2/2004 | Bystrom et al. |
| 6,790,178 B1 | 9/2004 | Mault et al. |
| 6,804,554 B2 | 10/2004 | Ujhelyi et al. |
| 6,827,695 B2 | 12/2004 | Palazzolo et al. |
| 6,865,413 B2 | 3/2005 | Halperin et al. |
| 6,908,437 B2 | 6/2005 | Bardy |
| 6,990,373 B2 | 1/2006 | Jayne et al. |
| 7,074,199 B2 | 7/2006 | Halperin et al. |
| 7,108,665 B2 | 9/2006 | Halperin et al. |
| 7,118,542 B2 | 10/2006 | Palazzolo et al. |
| 7,122,014 B2 | 10/2006 | Palazzolo et al. |
| 7,149,579 B1 | 12/2006 | Koh et al. |
| 7,177,684 B1 | 2/2007 | Kroll et al. |
| 7,194,300 B2 | 3/2007 | Korzinov |
| 7,220,235 B2 | 5/2007 | Geheb et al. |
| 7,277,752 B2 | 10/2007 | Matos |
| 7,295,871 B2 | 11/2007 | Halperin et al. |
| 7,340,296 B2 | 3/2008 | Stahmann et al. |
| 7,427,921 B2 | 9/2008 | Van Woudenberg |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,502,643 B2 | 3/2009 | Farringdon et al. |
| 7,602,947 B1 | 10/2009 | Lemelson et al. |
| 7,702,390 B1 | 4/2010 | Min |
| 7,717,855 B2 | 5/2010 | Caldarone et al. |
| 7,810,172 B2 | 10/2010 | Williams |
| 7,831,303 B2 | 11/2010 | Rueter et al. |
| 7,974,689 B2 | 7/2011 | Volpe et al. |
| 8,114,026 B2 | 2/2012 | Leschinsky et al. |
| 8,121,683 B2 | 2/2012 | Bucher et al. |
| 8,128,550 B2 | 3/2012 | Loeb et al. |
| 8,140,154 B2 | 3/2012 | Donnelly et al. |
| 8,246,548 B2 | 8/2012 | Naghavi et al. |
| 8,271,082 B2 | 9/2012 | Donnelly et al. |
| 8,369,944 B2 | 2/2013 | Macho et al. |
| 8,551,008 B2 | 10/2013 | Naghavi et al. |
| 8,600,486 B2 | 12/2013 | Kaib et al. |
| 8,649,861 B2 | 2/2014 | Donnelly et al. |
| 8,668,644 B2 | 3/2014 | Ong et al. |
| 8,706,215 B2 | 4/2014 | Kaib et al. |
| 8,753,283 B2 | 6/2014 | Leschinsky |
| 8,764,789 B2 | 7/2014 | Ganske et al. |
| 8,790,266 B2 | 7/2014 | Caldarone et al. |
| 8,795,323 B2 | 8/2014 | Leschinsky |
| 8,874,301 B1 | 10/2014 | Rao et al. |
| 8,904,214 B2 | 12/2014 | Volpe et al. |
| 8,909,335 B2 | 12/2014 | Radzelovage |
| 8,911,469 B2 | 12/2014 | Raheman |
| 8,932,220 B2 | 1/2015 | Ong et al. |
| 8,951,193 B2 | 2/2015 | Ong et al. |
| 8,956,387 B2 | 2/2015 | Naghavi et al. |
| 8,974,491 B2 | 3/2015 | Leschinsky |
| 8,986,342 B2 | 3/2015 | Naghavi et al. |
| 9,008,801 B2 | 4/2015 | Kaib et al. |
| 9,119,759 B2 | 9/2015 | Caldarone et al. |
| 9,128,484 B1 | 9/2015 | Doyle et al. |
| 9,135,398 B2 | 9/2015 | Kaib et al. |
| 9,205,019 B2 | 12/2015 | Ganske et al. |
| 9,295,429 B2 | 3/2016 | Ong et al. |
| 9,346,400 B2 | 5/2016 | Attard et al. |
| 9,398,859 B2 | 7/2016 | Volpe et al. |
| 9,420,957 B2 | 8/2016 | Ong et al. |
| 9,475,496 B2 | 10/2016 | Attard et al. |
| 9,610,213 B2 | 4/2017 | Leschinsky |
| 9,724,008 B2 | 8/2017 | Sullivan et al. |
| 2001/0010424 A1 | 8/2001 | Osmer et al. |
| 2002/0107435 A1 | 8/2002 | Swetlik et al. |
| 2003/0004547 A1 | 1/2003 | Owen et al. |
| 2003/0023277 A1 | 1/2003 | Owen et al. |
| 2003/0032988 A1 | 2/2003 | Fincke |
| 2003/0095648 A1 | 5/2003 | Kaib et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2003/0233129 A1 | 12/2003 | Matos |
| 2004/0007970 A1 | 1/2004 | Ma et al. |
| 2004/0049233 A1 | 3/2004 | Edwards |
| 2004/0064062 A1 | 4/2004 | Zhou et al. |
| 2004/0143297 A1 | 7/2004 | Ramsey |
| 2004/0215090 A1 | 10/2004 | Erkkila et al. |
| 2004/0267570 A1 | 12/2004 | Becker |

(56) References Cited

U.S. PATENT DOCUMENTS

| | | |
|---|---|---|
| 2005/0049515 A1 | 3/2005 | Misczynski et al. |
| 2005/0131465 A1 | 6/2005 | Freeman et al. |
| 2005/0165321 A1 | 7/2005 | Fischell et al. |
| 2005/0234354 A1 | 10/2005 | Rowlandson et al. |
| 2005/0234355 A1 | 10/2005 | Rowlandson et al. |
| 2006/0036292 A1 | 2/2006 | Smith et al. |
| 2006/0084883 A1 | 4/2006 | Linker |
| 2006/0085049 A1 | 4/2006 | Cory et al. |
| 2006/0129067 A1 | 6/2006 | Grajales et al. |
| 2006/0135881 A1* | 6/2006 | Giftakis ............... A61B 5/4094 600/544 |
| 2006/0178706 A1 | 8/2006 | Lisogurski et al. |
| 2006/0220809 A1 | 10/2006 | Stigall et al. |
| 2006/0234202 A1 | 10/2006 | Brown |
| 2006/0264776 A1 | 11/2006 | Stahmann et al. |
| 2006/0270952 A1 | 11/2006 | Freeman et al. |
| 2007/0073120 A1 | 3/2007 | Li et al. |
| 2007/0118056 A1 | 5/2007 | Wang et al. |
| 2007/0129769 A1 | 6/2007 | Bourget et al. |
| 2007/0161913 A1 | 7/2007 | Farrell et al. |
| 2007/0169364 A1 | 7/2007 | Townsend et al. |
| 2007/0208266 A1 | 9/2007 | Hadley |
| 2007/0239220 A1 | 10/2007 | Greenhut et al. |
| 2007/0265671 A1 | 11/2007 | Roberts et al. |
| 2007/0299474 A1 | 12/2007 | Brink |
| 2008/0004536 A1 | 1/2008 | Baxi et al. |
| 2008/0015454 A1 | 1/2008 | Gal |
| 2008/0030656 A1 | 2/2008 | Watson et al. |
| 2008/0031270 A1 | 2/2008 | Tran et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0167567 A1 | 7/2008 | Bashour et al. |
| 2008/0221631 A1 | 9/2008 | Dupelle |
| 2008/0249591 A1 | 10/2008 | Gaw et al. |
| 2008/0287770 A1 | 11/2008 | Kurzweil et al. |
| 2008/0306562 A1 | 12/2008 | Donnelly et al. |
| 2008/0312520 A1 | 12/2008 | Rowlandson et al. |
| 2008/0312709 A1 | 12/2008 | Volpe et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0082691 A1 | 3/2009 | Denison et al. |
| 2009/0093686 A1 | 4/2009 | Hu et al. |
| 2009/0093687 A1 | 4/2009 | Telfort et al. |
| 2009/0137884 A1 | 5/2009 | Naghavi et al. |
| 2009/0138059 A1 | 5/2009 | Ouwerkerk |
| 2009/0177100 A1 | 7/2009 | Ternes |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0287120 A1 | 11/2009 | Ferren et al. |
| 2009/0292194 A1 | 11/2009 | Libbus et al. |
| 2010/0030034 A1 | 2/2010 | Schulhauser et al. |
| 2010/0030293 A1 | 2/2010 | Sarkar et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0076533 A1 | 3/2010 | Dar et al. |
| 2010/0083968 A1 | 4/2010 | Wondka et al. |
| 2010/0179438 A1 | 7/2010 | Heneghan et al. |
| 2010/0222976 A1 | 9/2010 | Haug |
| 2010/0234715 A1 | 9/2010 | Shin et al. |
| 2010/0234716 A1 | 9/2010 | Engel |
| 2010/0292619 A1 | 11/2010 | Redington et al. |
| 2010/0295674 A1 | 11/2010 | Hsieh et al. |
| 2010/0298899 A1 | 11/2010 | Donnelly et al. |
| 2010/0312297 A1 | 12/2010 | Volpe et al. |
| 2011/0077728 A1 | 3/2011 | Li et al. |
| 2011/0190807 A1 | 8/2011 | Redington et al. |
| 2011/0196220 A1 | 8/2011 | Storm |
| 2011/0240043 A1 | 10/2011 | Redington |
| 2011/0251635 A1 | 10/2011 | Caldarone |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0144551 A1 | 6/2012 | Guldalian |
| 2012/0146797 A1 | 6/2012 | Oskin et al. |
| 2012/0158074 A1 | 6/2012 | Hall |
| 2012/0158075 A1 | 6/2012 | Kaib et al. |
| 2012/0265240 A1 | 10/2012 | Ganske et al. |
| 2012/0277789 A1 | 11/2012 | Caldarone et al. |
| 2013/0085538 A1* | 4/2013 | Volpe .................... A61B 5/742 607/6 |
| 2013/0087609 A1 | 4/2013 | Nichol et al. |
| 2013/0197924 A1 | 8/2013 | Kocis et al. |
| 2013/0197942 A1 | 8/2013 | Chiu et al. |
| 2013/0218196 A1 | 8/2013 | Chueng |
| 2013/0231711 A1* | 9/2013 | Kaib ...................... G16H 40/63 607/5 |
| 2013/0317581 A1 | 11/2013 | Redington |
| 2013/0325078 A1 | 12/2013 | Whiting et al. |
| 2013/0325096 A1 | 12/2013 | Dupelle et al. |
| 2014/0163334 A1 | 6/2014 | Volpe et al. |
| 2014/0257122 A1 | 9/2014 | Ong et al. |
| 2014/0296756 A1 | 10/2014 | Ganske et al. |
| 2014/0371806 A1 | 12/2014 | Raymond et al. |
| 2015/0005588 A1 | 1/2015 | Herken et al. |
| 2015/0018702 A1 | 1/2015 | Galloway et al. |
| 2015/0039053 A1 | 2/2015 | Kaib et al. |
| 2015/0066284 A1 | 3/2015 | Yopp |
| 2015/0088020 A1 | 3/2015 | Dreisbach et al. |
| 2015/0094552 A1 | 4/2015 | Golda et al. |
| 2015/0164349 A1 | 6/2015 | Gopalakrishnan et al. |
| 2015/0217121 A1 | 8/2015 | Subramanian et al. |
| 2015/0231403 A1 | 8/2015 | Kaib et al. |
| 2015/0257715 A1* | 9/2015 | Quan ................... A61B 5/0531 600/510 |
| 2015/0265286 A1 | 9/2015 | Raheman |
| 2015/0265845 A1* | 9/2015 | Sullivan ................ A61B 5/053 607/8 |
| 2015/0342489 A1 | 12/2015 | Bhaumik et al. |
| 2015/0352367 A1* | 12/2015 | Quan ................... A61B 5/7253 601/41 |
| 2016/0120430 A1 | 5/2016 | Bayasi et al. |
| 2016/0135706 A1* | 5/2016 | Sullivan ................ A61B 5/1118 600/301 |
| 2016/0143585 A1 | 5/2016 | Donnelly et al. |
| 2016/0270738 A1* | 9/2016 | Volpe ....................... A61B 5/08 |
| 2016/0284038 A1* | 9/2016 | Johnson ............... G06Q 50/265 |
| 2016/0342761 A1* | 11/2016 | Whiting ................ G16H 10/60 |
| 2017/0003356 A1* | 1/2017 | Kaib ..................... A61B 5/6805 |
| 2017/0056650 A1* | 3/2017 | Cohen .................. A61B 5/0408 |
| 2017/0087371 A1 | 3/2017 | Freeman et al. |
| 2017/0108862 A1* | 4/2017 | Mikkelsen ........... G05D 1/0016 |
| 2017/0143977 A1* | 5/2017 | Kaib ....................... A61N 1/046 |
| 2017/0225001 A1* | 8/2017 | Zaidi .................... A61B 5/0464 |
| 2017/0281462 A1 | 10/2017 | Freeman et al. |
| 2018/0055442 A1* | 3/2018 | Freeman ............... A61N 1/3993 |
| 2018/0110667 A1* | 4/2018 | Freeman ................ A61G 13/08 |
| 2018/0272147 A1* | 9/2018 | Freeman ............... A61N 1/3629 |

FOREIGN PATENT DOCUMENTS

| | | |
|---|---|---|
| CN | 101848677 A | 9/2010 |
| DE | 2644236 C3 | 4/1981 |

(56) References Cited

FOREIGN PATENT DOCUMENTS

| | | |
|---|---|---|
| EP | 0295497 B1 | 9/1993 |
| EP | 0335356 B1 | 3/1996 |
| EP | 1642616 A2 | 4/2006 |
| EP | 1455640 B1 | 1/2008 |
| EP | 1720446 B1 | 7/2010 |
| JP | S6368135 A | 3/1988 |
| JP | 5115450 A | 5/1993 |
| JP | H07541 A | 1/1995 |
| JP | H10-28679 A | 2/1998 |
| JP | H11319119 A | 11/1999 |
| JP | 2002-102361 A | 4/2002 |
| JP | 2002-514107 A | 5/2002 |
| JP | 2002200059 A | 7/2002 |
| JP | 2002534231 A | 10/2002 |
| JP | 2003235997 A | 8/2003 |
| JP | 2004538066 A | 12/2004 |
| JP | 2005275606 A | 10/2005 |
| JP | 2007531592 A | 11/2007 |
| JP | 2008302228 A | 12/2008 |
| JP | 2009510276 A | 3/2009 |
| JP | 2009518057 A | 5/2009 |
| JP | 2009528909 A | 8/2009 |
| JP | 2010-508128 A | 3/2010 |
| JP | 2010530114 A | 9/2010 |
| WO | 200002484 A1 | 1/2000 |
| WO | 2004054656 A1 | 7/2004 |
| WO | 2004067083 A2 | 8/2004 |
| WO | 2005082454 A1 | 9/2005 |
| WO | 2006050235 A1 | 5/2006 |
| WO | 2007019325 A2 | 2/2007 |
| WO | 20070057169 A1 | 5/2007 |
| WO | 2007077997 A1 | 7/2007 |
| WO | 2008137286 A1 | 11/2008 |
| WO | 2009034506 A1 | 3/2009 |
| WO | 2010014497 A1 | 2/2010 |
| WO | 2010025432 A1 | 3/2010 |
| WO | 2014140832 A2 | 9/2014 |
| WO | 2014167422 A2 | 10/2014 |
| WO | 2014167423 A2 | 10/2014 |
| WO | 2014199239 A2 | 12/2014 |
| WO | 2015127466 A2 | 8/2015 |

OTHER PUBLICATIONS

Phys.org, Could Your Car Predict a Cardiac Event? Team Explores Heart Monitoring in Vehicles. https://www.mdtmag.com/news/2017/06/could-your-car-predict-cardiac-event-team-explores-heart-monitoring-vehicles, Jun. 8, 2017, 5 pages.

Asahi Kasei Corp., Press Release—Completion of Asahi Kasei's drivable concept car AKZY(TM), May 17, 2017, 3 pages.

Hristov, Luben, Capacitive Proximity Detection in the Automotive Industry, www.atmel.com, 2010, 3 pages.

Wang, David, Texas Instruments—Application Report—Capacitive Proximity Sensing Using the FDC1004, SNOA928A, Mar. 2015—Revised Apr. 2015, 10 pages.

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/full/166/1/111.

O'Keeffe et al., "Reproducability and responsiveness of quality of life assessment and six minute walk test in elderly heart failure patients", Heart (1998) 80: 377-382.

* cited by examiner

VEHICLE COMPATIBLE AMBULATORY DEFIBRILLATOR

CROSS-REFERENCE TO RELATED APPLICATIONS

This application claims priority under 35 U.S.C. § 119 to U.S. Patent Application No. 62/515,563 filed on Jun. 6, 2017. All subject matter set forth in the above referenced application is hereby incorporated by reference in its entirety into the present application as if fully set forth herein.

BACKGROUND

This disclosure relates to systems and techniques for changing an operating mode of a medical device.

There are a wide variety of electronic and mechanical devices for monitoring and treating patients' medical conditions. In some examples, depending on the underlying medical condition being monitored and/or treated, medical devices such as cardiac pacemakers or defibrillators may be surgically implanted or connected externally to the patient. For example, the medical condition may be a cardiac arrhythmia. In some cases, physicians may use medical devices alone or in combination with drug therapies to treat patient medical conditions.

One example of a cardiac arrhythmia is ventricular fibrillation. Ventricular fibrillation occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia.

Implantable or external pacemakers and defibrillators, such as automated external defibrillators (AEDs), have significantly improved the ability to treat these potentially life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator.

An ambulatory defibrillator is an example of an external defibrillator. The ambulatory defibrillator may provide the capability of substantially continuously monitoring the patient's heart through one or more sensing electrodes for treatable arrhythmias. When a treatable arrhythmia occurs, the ambulatory defibrillator may apply corrective electrical pulses directly to the heart through one or more therapy electrodes.

SUMMARY

An example of an ambulatory medical device according to the disclosure includes one or more sensing electrodes configured to sense cardiopulmonary signals of a patient, a network interface, and one or more processors configured to receive signals from one or more vehicle occupancy sensors, detect usage of the ambulatory medical device in a vehicle based on the received signals from the one or more vehicle occupancy sensors, detect at least one of a medical event and a medical premonitory event of the patient based on the sensed cardiopulmonary signals, and provide driving control information to the vehicle, via the network interface, based at least in part on the detected usage of the ambulatory medical device in the vehicle and the detected at least one of the medical event and the medical premonitory event.

Implementations of such a device may include one or more of the following features. The driving control information provided to the vehicle may include driving control messages. The one or more processors may be configured to provide the driving control messages to an autonomous driving controller via the network interface. The driving control messages may include one or more of steering, acceleration, and braking messages. The driving control messages may include autonomous driving control messages. The driving control information may include navigation instructions. The navigation instructions may include a request to change a navigation destination based on the detected at least one of the medical event and the medical premonitory event. The received signals from the one or more vehicle occupancy sensors may be indicative of a patient position in the vehicle. The driving control information provided to the vehicle may be based at least in part on the patient position in the vehicle. The one or more processors may be configured to provide, via the network interface, one or more of notifications and alarms to a vehicle user interface disposed in the vehicle. The notifications may include one or more of an instruction to transfer patient data to emergency medical services and an instruction for a vehicle communications unit to connect to an emergency medical services communication network. The at least one of the medical event and the medical premonitory event may include a cardiac event. The one or more vehicle occupancy sensors may be disposed in the vehicle and the one or more processors may be communicatively coupled, via the network interface, to the one or more vehicle occupancy sensors that are disposed in the vehicle. The one or more vehicle occupancy sensors may be disposed on the ambulatory medical device and may be configured to determine that the ambulatory medical device is in the vehicle. The ambulatory medical device may include therapy electrodes in communication with the one or more processors. The one or more processors may be configured to adjust one or more therapy delivery parameters based on the detected usage of the ambulatory medical device in the vehicle. The one or more therapy delivery parameters may include a time delay before delivery of a therapeutic shock. The therapy electrodes may be configured to deliver defibrillation current. The therapy electrodes may be configured to deliver pacing pulses. The one or more processors may be configured to determine a geo-location of the ambulatory medical device. The one or more processors may be configured to determine navigation instructions based at least in part on the geo-location of the ambulatory medical device. The ambulatory medical device may include a location module configured to send one or more signals indicative of the geo-location of the ambulatory medical device to the one or more processors. The one or more processors may be configured to determine the geo-location of the ambulatory medical device based on the one or more signals from the location module. The one or more processors may be configured to receive geo-location information from the vehicle and to determine the geo-location of the ambulatory medical device based on the geo-location information from the vehicle. The ambulatory medical device may include an audio interface configured to receive and provide audible information. The cardiopulmonary signals of the patient may include one or more of an electrocardiogram (ECG), a heart rate, and a blood pressure. The one or more processors may be configured to detect the medical premonitory event and determine an event estimation of risk score associated with the detected medical premonitory event for a particular time period. The one or more processors may be configured to provide the driving control information to the vehicle based on the event estimation of risk score exceeding a risk score threshold for the particular time period. The particular time period may be 1-60 minutes from the detection of the medical premonitory event. The driving control information may include an instruction to pull the vehicle out of traffic. The particular time period may be one of 1-59 minutes from the detection of the medical premonitory event and 1-24 hours from the detection of the medical premonitory event. The driving control information may include an instruction to alter at least a portion of a programmed trip itinerary.

Items and/or techniques described herein may provide one or more of the following capabilities. An ambulatory medical device, which may be a wearable medical device, includes sensing electrodes that monitor physiological signals, including cardiopulmonary signals, for a patient associated with the ambulatory medical device. Based on the monitored physiological signals, the ambulatory medical device may detect a current medical event (ME) such as a cardiac event and/or may detect a predicted elevated risk for a future ME, also referred to as a medical premonitory event. The ambulatory medical device may also determine that the patient using the device is in a vehicle, for example a self-driving car, based on signals from vehicle occupancy sensors on the medical device and/or in and/or on the vehicle. These sensors may also determine whether the patient is a driver of the vehicle or the passenger. The ambulatory medical device may establish communications with the vehicle and may exchange information with the vehicle. For example, the vehicle may provide seat occupancy information, navigation information and/or driving condition information (e.g., speed, lane position, etc.) to the medical device. The medical device may provide patient information and detected and/or predicted ME information to the vehicle. In case of a current or predicted emergency ME, the medical device may further provide notifications and/or recommendations to the vehicle. The notifications may be information that is helpful to the patient and/or another occupant of the vehicle in case of the medical emergency. For example, the information may include a description of the medical emergency and/or an alarm indicating an upcoming defibrillation treatment. As further examples, the messages may be driving control commands or recommendations in response to which the vehicle may move out of traffic, stop, and/or navigate to a medical facility.

Other capabilities may be provided and not every implementation according to the disclosure must provide any, let alone all, of the capabilities discussed. Further, it may be possible for an effect noted above to be achieved by means other than that noted and a noted item/technique may not necessarily yield the noted effect.

DESCRIPTION OF DRAWINGS

The accompanying drawings are not intended to be drawn to scale. In the drawings, components that are identical or nearly identical may be represented by a like numeral. For purposes of clarity, not every component is labeled in every drawing.

DETAILED DESCRIPTION

Figure 1A:
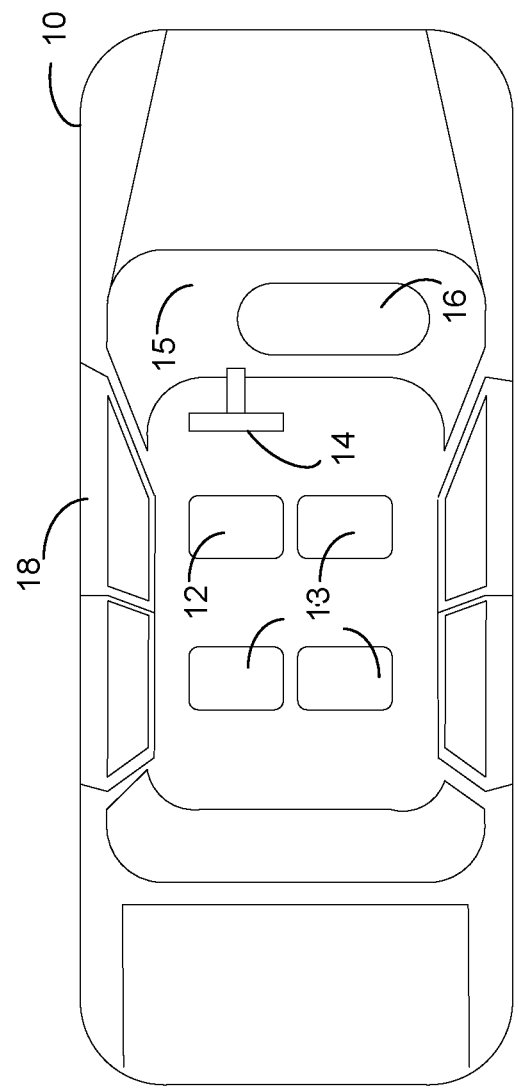
FIGS. 1A-1C are schematic diagrams of a vehicle in accordance with embodiments of the present disclosure.

A medical device for use with the systems and techniques as disclosed herein may be configured to monitor one or more cardiopulmonary signals of a patient and determine whether the patient may be experiencing a cardiac condition. For example, the medical device may be an ambulatory medical device and may include a plurality of sensing electrodes that are disposed at various locations on the patient's body and configured to sense or monitor the cardiopulmonary signals of the patient. The ambulatory medical device may be configured as a wearable medical device for use by the patient during routine activities, such as in riding and/or operating a vehicle and discussed further herein. In some implementations, the medical device can be configured to monitor, in addition to cardiopulmonary signals, other physiological parameters as described in further detail below. The medical device can be used as a cardiac monitor in certain cardiac monitoring applications, such as mobile cardiac telemetry (MCT) and/or continuous event monitoring (CEM) applications.

When the ambulatory medical device is being worn by the patient in the vehicle, the medical device and the vehicle may have components that enable a communicative connection to be established (e.g., via one or more pre-configured operating modes of the medical device and/or vehicle). This connection may result in operations of the medical device and/or the vehicle to be adjusted. Such operations may be advantageous, for example, in modifying the parameters under which a medical event may be detected or predicted so as to be more suitable for a vehicle environment. Operations may further include alerting the patient or other occupants within the vehicle that the patient may be at an elevated risk of a potential medical event. When such a determination of elevated risk is made, the vehicle may be able to provide countermeasures for addressing the situation, such as providing relevant alarms and/or notices of the potential or present medical event to vehicle occupants or appropriate medical and/or emergency personnel, information regarding how to treat or provide care for the patient, information for operating the vehicle (e.g., directions to nearest hospital or treatment center), control of the vehicle (e.g., redirecting the destination in the case of an autonomous vehicle), amongst others. The manner in which operations of the medical device and the vehicle when the communicative connection is established will be discussed in further detail herein.

Referring back to the medical device itself, the medical device may be configured to evaluate the monitored patient signals along with various detection parameters, criteria and/or conditions (e.g., patient thresholds) that, if met, may indicate that the patient is experiencing or will soon experience a medical condition. Based on the indication of the medical condition, the medical device may be configured to determine an appropriate treatment for the patient based on the sensed cardiopulmonary signals and cause one or more therapeutic shocks (e.g., defibrillating and/or pacing shocks) to be delivered to the body of the patient. The medical device may include a plurality of therapy electrodes that are disposed at various locations on the patient's body and configured to deliver the therapeutic shocks.

The medical device as described herein can be configured to monitor a patient for arrhythmia conditions such as bradycardia, ventricular tachycardia (VT) and/or ventricular fibrillation (VF). The detection methods and systems described hereinafter are disclosed as detecting VT and VF as examples only and not limiting of the disclosure. Other arrhythmias, such as, but not limited to, atrial arrhythmias such as premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventricle arrhythmias such as premature ventricular contractions (PVCs) and accelerated idioventricular rhythm, may also be detected. In some implementations (e.g., implementations in which the medical device is a treatment device, such as a pacing and/or a defibrillating device), if an arrhythmia condition is detected, the medical device may automatically provide a therapeutic treatment for the condition such as, for example, a pacing pulse, a defibrillation shock, and/or a tactile, electrical and/or audible sensory stimulation.

In some implementations, the medical device as described herein may be configured to monitor a patient presenting with syncope (e.g., by analyzing the patient's cardiac activity for aberrant patterns that can indicate abnormal physiological function and/or based on blood pressure measurements). In some examples, aberrant patterns may occur prior to, during, or after the onset of syncope symptoms. Cardiopulmonary signals are any physiological signal that provides information related to the functioning of the patient's cardiopulmonary system (heart/lungs/circulation), which may include, but are not limited to, an electrocardiogram (ECG), impedance respiration, blood pressure, blood flow.

Figure 2A:
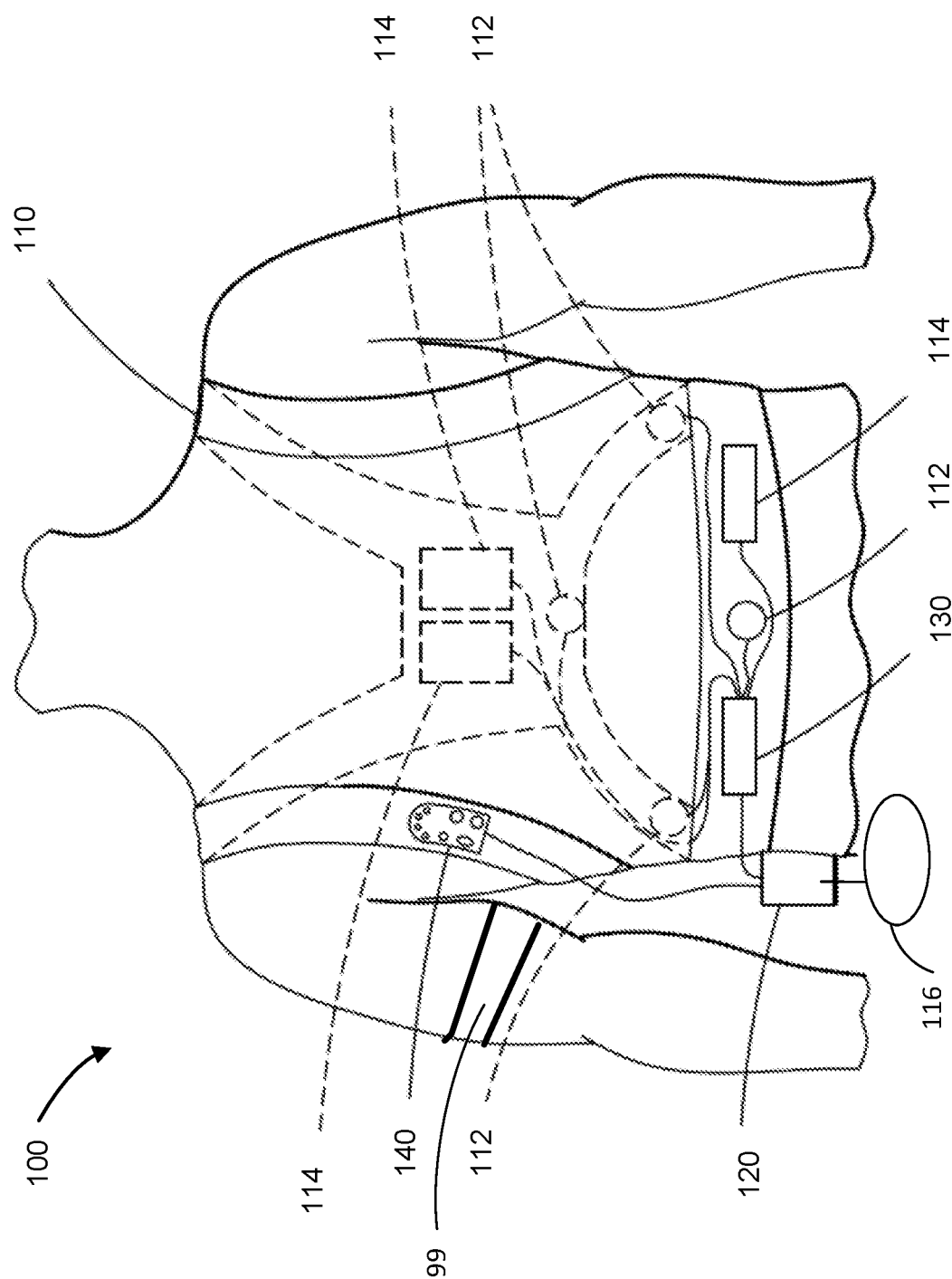
FIG. 2A is an example of a wearable medical device in accordance with embodiments of the present disclosure.

Sudden drops in blood pressure may be indicative of syncope, often referred to as fainting. Referring briefly to FIG. 2A, in an implementation, the wearable medical device 100 may include or may be coupled to a blood pressure cuff 99. The blood pressure cuff 99 is configured to be positioned about a limb of the patient and to contract about the limb when actuated. In order to use the blood pressure cuff 99, the patient and/or a caregiver wraps the blood pressure cuff 99 around the limb and fastens the blood pressure cuff 99 so that it fits snuggly around the limb. The blood pressure cuff 99 is coupled to a cuff controller and a gas source configured to inflate and deflate the blood pressure cuff 99. The blood pressure cuff 99 may include one or more attachment sections and an inflatable section. The attachment sections and are non-inflatable and are configured to secure the blood pressure cuff 99 around the limb of the patient. The attachment sections and may include for example elastic straps, hook and loop fasteners, buckles, etc. In an implementation, the blood pressure cuff 99 may include an adhesive surface to couple the blood pressure cuff 99 to the patient's limb.

The inflatable section includes a cuff bladder disposed inside of a cuff sleeve that receives a fluid, such as air or other gas, to cause the cuff expand and retract about the patient's limb. The bladder is constructed of an air impermeable material, such as flexible plastic or rubber. Although the illustrated implementation includes a single bladder positioned within a cuff, it is to be appreciated that other implementations are also possible. By way of example, according to some implementations, the fabric sleeve may itself be air impermeable, such that no separate bladder is required. In other implementations, multiple, separate inflatable bladders may be incorporated into a common sleeve, as aspects of the present invention are not limited in this respect. In an implementation, the cuff sleeve may itself be air impermeable, such that no separate bladder is required. Alternatively, the cuff sleeve may include a microporous fabric and, therefore, require the separate bladder. Dimensions of the blood pressure cuff 99 (e.g., length L and width W) may generally follow established standards established for blood pressure measurement cuffs. In various implementations, the dimensions of the blood pressure cuff 99 may be larger or smaller than standard dimensions for the blood pressure cuff. Standard dimensions for the blood pressure cuff may apply to arm cuffs. The blood pressure cuff includes a connection port at one end of the bladder to allow air to enter the bladder from the gas source during inflation and to exit the bladder during deflation. In an implementation, the blood pressure cuff 99 may include one or more blood pressure sensors configured to monitor the limb for the onset of Korotkoff sounds or vibrations. In an implementation, the blood pressure cuff 99 may include an electrical coupling to the cuff controller. The cuff controller may receive signals indicative of blood pressure measurements as determined by the blood pressure measurement device and/or signals from the one or more blood pressure sensors via the electrical coupling. The cuff controller may send these signals to the medical device controller 120. In an implementation, the ME detector 324 may detect syncope based on one or more of the blood pressure measurements (i.e., the sudden reduction in blood pressure) and the patient's posture in the seat of the vehicle (e.g., as detected by a tilt/accelerometer sensor). For example, if the patient is slumped in the seat of the vehicle 10 in conjunction with a drop in blood pressure, then the ME detector 324 may detect syncope.

In some implementations, the medical device may be configured to dynamically and/or adaptively change an operating mode of the medical device based on an operating environment for the patient. Dynamically and/or adaptively adjusting the operating mode includes adjusting the operating mode in substantially real-time. The operating mode may be a default operating mode. The default operating mode may be the operating mode for general usage by the patient. In contrast, as described in further detail herein, the operating mode may be a vehicle operating mode. In the vehicle operating mode, operations of the medical device are tailored for the vehicle operating environment. In the vehicle operating mode, the wearable medical device may communicate with the vehicle based on predicted and/or detected MEs of the patient. Optionally, in the vehicle operation mode, the wearable medical device may adjust its own operations with regard to ME detection/prediction and/or therapy delivery based on the presence of the wearable medical device in the vehicle.

The patient wearing the medical device may get into and travel in a vehicle as either a driver or a passenger. For example, the vehicle may be a passenger or commercial car, truck, sport utility vehicle, taxi, bus, etc. Operations of the medical device while in the vehicle operating mode may include, for example, changing therapy delivery parameters (e.g., delay time and requirement to confirm various vehicle conditions prior to therapy delivery), adjusting ME detection due to vehicle conditions such as vibrations or audible noise, and/or interacting with one or more vehicle sensors and/or vehicle driving controls (e.g., providing information to the vehicle such as notifications, alarms, and/or driving control messages, receiving information from the vehicle, etc.) based on patient medical conditions determined by the medical device. For example, the vehicle operating mode may disable delivery of a therapeutic shock for a driver unless the car is stopped and out of traffic. As another example, the vehicle operating mode may trigger instructions or warnings from the vehicle that the driver should proceed to a hospital and/or may trigger notification of emergency rescuers. As a further example, in the vehicle operating mode, the medical device may provide driving control messages to the vehicle 10. In various implementations, the driving control messages may be commands or recommendations for an autonomous driving controller. The autonomous driving controller determines a response or action of the vehicle in response to the driving control messages (e.g., the commands or recommendations).

In an implementation, the medical device may select the vehicle operating mode based on a selection input provided to the medical device (e.g., by the patient, caregiver, or bystander). Alternatively or additionally, the medical device may be configured to select the vehicle operating mode based on information received from or exchanged with the operating environment (i.e., the vehicle).

The vehicle operating mode may enable safer delivery of therapy, faster and more efficient treatment by hospital personnel, and/or faster location of the vehicle by emergency medical responders. The vehicle operating mode may facilitate treatment of the patient by the responders by making the vehicle easier to access and/or find. Further, the vehicle operating mode may provide timely information to occupants of the vehicle other than the patient. These occupants may aid the patient and/or control the car if the driver is disabled or in danger of experiencing a medical condition. The vehicle operating mode may enable the medical device to effect changes in the operation of the vehicle so that the vehicle does not crash or otherwise endanger other vehicles as a result of a medical emergency occurring inside the vehicle, particularly if the wearer of the medical device is the driver of the vehicle. Changes to the operation of the vehicle may include controlling and/or changing one or more of steering, acceleration, navigation, information provided to vehicle occupants via a vehicle user interface, and information provided to communication and/or medical devices external to the vehicle. These changes may occur based on and in response to a change in vehicle control from a manual or semi-autonomous driving mode to a fully autonomous driving mode.

Additionally, the medical device may provide the capability to estimate a risk of future MEs. Based on this estimated risk, in the vehicle operating mode, the medical device provide instructions and/or recommendations to an vehicle user interface and/or an autonomous driving controller such that the vehicle is stopped, slowed, out-of-traffic, on route to a medical facility, or arrived at a medical facility prior to the occurrence of any ME. In this way, the patient may not endanger herself or others by operating and/or being confined in a vehicle during the ME. The instructions and/or recommendations may vary based on whether the medical device detects an ME or a future ME, also referred to as a medical premonitory event. Further the instructions and/or recommendations may depend on a particular time period associated with an event estimation of risk score for the medical premonitory event.

By modifying vehicle operation, for instance taking control of steering and acceleration, in advance of the treatment of a passenger, the driver is made aware of the impending treatment event and may potentially help the passenger while the vehicle is still in motion. Further, the vehicle coordinates may be provided to an EMS dispatch system while the vehicle is still on route to the hospital emergency room and the EMS ambulance may be routed to intercept the vehicle on the way to the hospital to significantly improve both response time as well as quality of treatment of the patient.

The wearable medical device in communication with the vehicle may provide advantages over other defibrillation treatment devices. For instance, implanted cardioverter/defibrillators (ICDs) have the difficulty that if they detect a life-threatening rhythm of a patient's heart while the patient is driving, the ICD may deliver a defibrillation shock without warning that in some cases may actually cause the patient to lose control of the vehicle and crash if they happen to be driving, thus putting both the driver as well as other drivers as well as pedestrians in the immediate vicinity at risk of bodily harm, and in some cases, death.

The prediction of a future ME, e.g., the medical premonitory event, allows for tailoring of controls (depending on the type of patient and other factors, controls of the device may be pre-configured), messaging, user interfaces, and therapy based on a determined level of risk for the medical premonitory event at a particular time. For example, the wearable medical device may be situationally aware (e.g., the wearable medical device may be in the vehicle operating mode based on the detected use of the wearable medical device 100 in the vehicle 10). Further, in the example of the situationally aware wearable medical device, the wearable medical device 100 may determine that it is in use in an autonomous vehicle (e.g., via close proximity range sensors) and may determine the patient's role in the vehicle (e.g., the role as the driver or the passenger by virtue of where the wearable medical device is located while the vehicle is in motion). In such a situation, the wearable medical device 100 may take control of (e.g., issue a command and/or a message to the autonomous driving controller 50), for example, steering, acceleration, and/or braking of the vehicle 10 to safely guide the vehicle 10. Such guidance may prevent accidents due to a medical emergency associated with the driver. In such an example, even with moderate specificity, a quick-screen type of ME predictor may help the patient plan near-term activities, such as driving the vehicle 10, in which the patient may not be protected from deleterious effects of the ME. The wearable medical device 100 may send the command and/or message to the autonomous vehicle. The command and/or message may include an alert that the patient may soon be unable to control the vehicle 10 and that that vehicle 10 should take control of the vehicle 10 and navigate to, for example, the side of the road, the nearest appropriate medical facility.

Figure 1B:
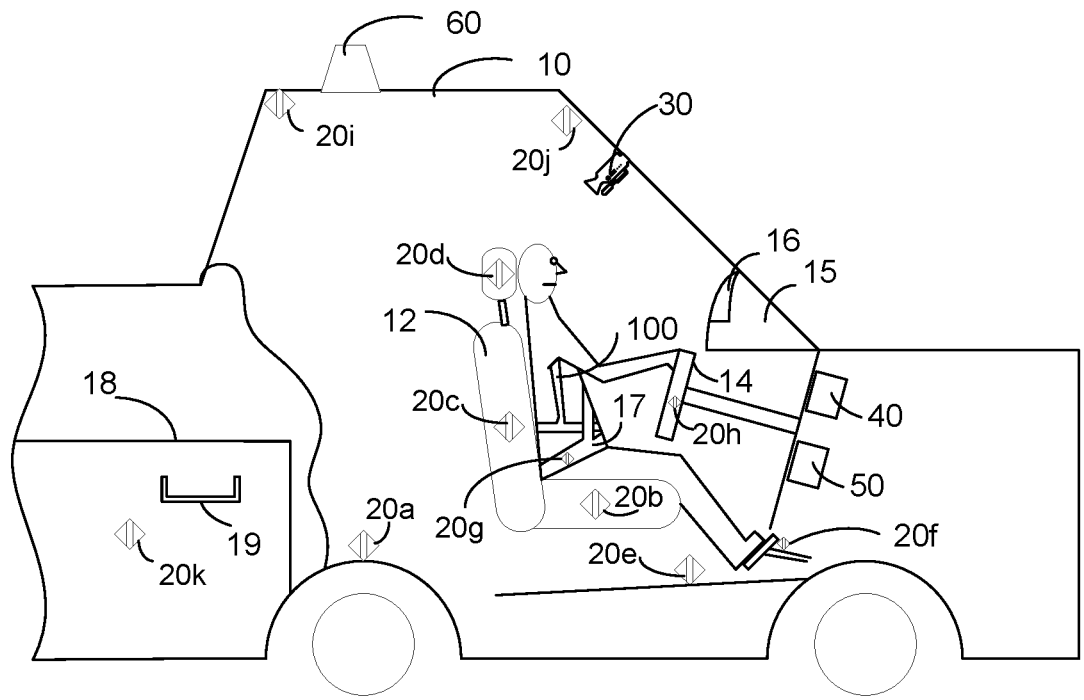
Figure 1C:
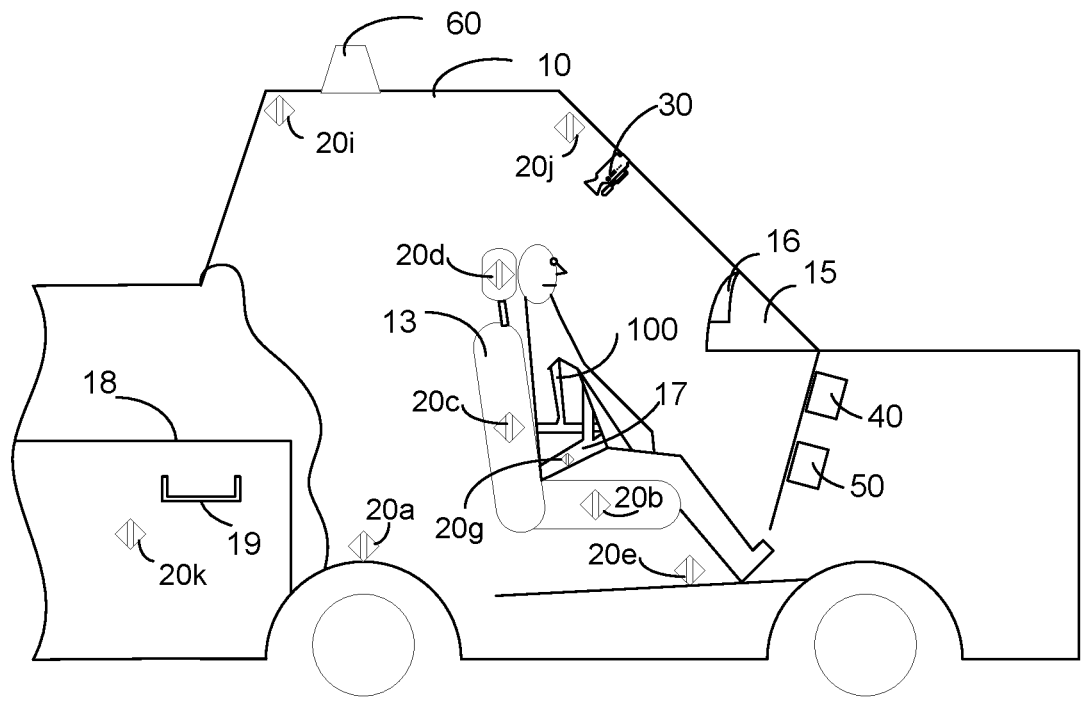

Referring to FIGS. 1A-1C, schematic diagrams of a vehicle are shown. The vehicle 10 includes a driver's seat 12 and passenger seats 13. The number of each type of seat and position in the vehicle 10 are examples only and not limiting of the disclosure. The driver's seat 12 is positioned for access to the steering wheel 14. The vehicle 10 also includes a dashboard 15 with an optional vehicle user interface 16. The vehicle user interface 16 may include push buttons, dials, voice activated systems, one or more touch screens, a display, lights, a speaker, a microphone, and/or other input/output devices. The driver input captured by the vehicle user interface 16 may include navigation information. For example, a driver, passenger, or other user of the vehicle user interface 16 may input a trip destination and/or a route. The input trip destination and/or route may constitute a programmed destination and/or route. As another example, the driver, passenger, or other user of the vehicle user interface 16 may input a trip itinerary which may include one or more destinations, one or more routes, one or more travel dates, and/or one or more travel times. The input trip itinerary may constitute a programmed trip itinerary. The vehicle user interface 16 may also provide visual or acoustic driver feedback. The vehicle 10 further includes at least one door 18.

The patient may be the driver or operator of the vehicle 10 and seated in the driver's seat 12 during operation of the vehicle 10 as shown schematically in FIG. 1B. Alternatively, the patient may be the passenger in the vehicle 10 and seated in the passenger's seat 13 during operation of the vehicle 10 as shown schematically in FIG. 1C. The patient may wear a wearable medical device 100 while operating or riding in the vehicle 10.

The vehicle 10 may include a vehicle sensor monitor 40. The vehicle sensor monitor 40 may communicate, via one or more wired and/or wireless connections, with one or more vehicle sensors 20a, 20b, 20c, 20d, 20e, 20f, 20g, 20h, 20i, 20j, and 20k. The one or more vehicle sensors 20a-20k are configured to detect one or more of the presence of occupants in the vehicle 10 and physiological parameters for the occupants. Thus one or more of the vehicle sensors 2a-20k may be vehicle occupancy sensors. The quantity, type, and positions of the vehicle sensors as shown in FIGS. 1B and 1C are examples only and not limiting of the disclosure. The one or more vehicle sensors may include, for example, contact sensors, torque sensors, force sensors, motion sensors, accelerometers, resistive potentiometers, differential transformers, humidity sensors, temperature sensors, pressure sensors, position sensors, shock sensors, piezo sensors, strain gauges, optical sensors, moving coil sensors, imaging sensors, electro-optical sensors, sound sensors, microphones, ultrasonic sensors, radiation sensors, flow sensors, radar sensors, lidar sensors, photoelectric sensors, inductive sensors, capacitive sensors, infrared proximity detectors, electromechanical sensors, and combinations thereof. All or a portion of the one or more vehicle sensors may be configured to sense and provide signals to the vehicle sensor monitor 40 indicative of physiological parameters including, but not limited to, cardiac parameters (e.g., electrocardiogram (ECG), pulse rate, heart rate), facial biometrics, eye opening conditions, respiration parameters, etc. The vehicle sensors may be built into the vehicle and/or may be driver-supplied devices (e.g., after market accessories).

The one or more vehicle sensors may include, for example, one or more vehicle motion sensors 20a, seat sensors 20b, 20c, and 20d, one or more leg area sensors 20e and 20f, one or more seat belt sensors 20 g, one or more steering wheel sensors 20h, and a temperature sensor 20i. The seat sensors 20b, 20c, and 20d may be components of an after-market vehicle accessory and/or may be installed in one or more of the vehicle seat cushion, the backrest and the headrest of the driver's seat and/or the passenger seats. The seat sensors 20b, 20c, and 20d may detect seat occupancy and/or the physiological parameters of the occupant which may include a weight of the occupant. The leg area sensors 20e and 20f may be situated in the passenger compartment so as to reliably detect the presence of the driver and/or the passenger. For example, the leg area sensors 20e and 20f may be installed, for example, in the floor mats, the brake and/or gas pedals, the doors or other locations on the frame or body of the vehicle 10. The seat or leg sensors may employ capacitive proximity detection such as the FDC1004 (Texas Instruments). The seat belt sensor 20g may be installed in the seat belt 17 or the seat belt engagement mechanism (not shown). The seat belt sensor 20g may be configured to measure the extension length via optical or magnetic encoding of the take-up spool of the seat belt 17 and/or to sense engagement of the seat belt attachment mechanism. In an implementation, the medical device controller 120 may determine height and/or weight of the patient based in part on the seatbelt extension measurements by the seat belt sensor 20g. The steering wheel sensor 20h is configured to detect the presence of the driver's hands on the steering wheel and/or to measure physiological parameters such as, for example cardiac and/or respiratory parameters via impedance cardiography or pneumography or electrocardiography, known to those skilled in the art. Driver hand presence may also be detected by capacitive proximity sensing such as discussed above. Some of the sensors may be built into the vehicle 10, while others may be placed in the vehicle 10 by the owner and/or the patient. Such examples would include a seat back cover with sensors built into it, or a clip-on device to be attached to the steering wheel. These add-ons may be self-contained and battery powered or be plugged into the power of the car, for instance via a wired USB connection. If the add-ons are wired into the car via USB, they may also communicate with the vehicle 10 by USB or other wired communication protocol, e.g. RS232, etc.

In an implementation, the one or more vehicle sensors may further include a seat position sensor (not shown). The medical device controller 120 may infer a height of the seat occupant based on a seat position as detected by the seat position sensor. In an implementation, the one or more vehicle sensors may determine a body position of the occupant of a seat (e.g., sitting straight or slumped). In an implementation, the wearable medical device 100 may include a sensor, for example, a tilt/accelerometer sensor on the patient that detects whether the patient is slumped over and may communicate this information to the vehicle 10. In an implementation, the one or more vehicle sensors may detect a distracted and/or sleeping driver. For example, the camera 30 may detect the driver activities or where the driver is looking. In response, the vehicle sensor monitor 40 may notify the medical device controller 120 and the medical device controller 120 may generate a vibration or alarm to wake up and/or re-focus the driver.

The one or more vehicle sensors may include a wireless communication device 20j. The wireless communication device 20j may enable Wi-Fi, Bluetooth®, satellite, and/or cellular communications capabilities for the vehicle 10. The satellite and/or cellular communications capabilities may include geo-location determination capabilities (e.g., via a global positioning system (GPS) and/or a cellular network positioning system). In an implementation, the wireless communication device 20j may communicate a vehicle geo-location to the wearable medical device 100. In such an implementation, the processor 318 may estimate the geo-location of the wearable medical device 100 as the vehicle's geo-location. The wireless communication device 20j is shown in FIGS. 1b and 1c as a discrete device as an example only and may be part of another component of the vehicle 10. When the patient wearing the wearable medical device 100 enters the vehicle 10, the wireless communication device 20*j* may establish communications with the wearable medical device 100. In various implementations, communications may be initiated by the wearable medical device 100 (e.g., via a network interface 306 of the wearable medical device 100 as discussed below) and/or by the wireless communication device 20*j* of the vehicle 10. Wireless communications between the wearable medical device 100 and the vehicle 10 may be via wireless communication such as Bluetooth®, or wireless standards such as 802.11, ZigBee®, etc. The vehicle 10 may communicate its capabilities such as autonomous braking and/or steering and/or acceleration and/or navigation to the wearable medical device 100. The vehicle 10 may also communicate its ability to communicate with outside resources such as emergency medical services, OnStar®, 911, emergency dispatch, etc., and the particular type of communication network (e.g. cellular and/or satellite). The wearable medical device 100 may communicate its functions and capabilities to the vehicle 10, including, for example, various physiological monitoring parameters, patient information, medical device operating parameters and/or specifications, communications bandwidth, data formats, etc.

The vehicle sensor monitor 40 may further communicate, via a wired and/or wireless connection, with a passenger compartment camera 30. The camera 30 may include appropriate image analysis capabilities for detecting the position of the driver, the position of the passenger, the presence of the driver in the driver's seat, and/or the presence of a passenger in a passenger's seat. The camera 30 may further provide data indicative of facial biometrics for identification purposes and/or for physiological assessment purposes. In an implementation, the wearable medical device 100 may include an identification code (e.g., a serial number, a bar code, a two-dimensional bar code, a quick response code, etc.). The camera 30 may be configured to detect the identification code. Based in part on the detection of the identification code, the autonomous driving controller 50 and/or the medical device controller 120 may identify the patient and/or determine the position of the patient in the vehicle 10 (e.g., driver or passenger). The one or more vehicle sensors 20*a*-20*g* and/or the camera 30 may monitor the occupants of the vehicle substantially continuously or at pre-determined intervals and may monitor the occupants when the car is traveling and/or stopped.

In an implementation, the one or more vehicle sensors may include one or more proximity detectors 20*k*. For example, an exterior handle 19 on a vehicle door 18 may include one or more proximity detectors 20*k*. In an implementation, other areas of the vehicle 10, such as, for example, the seats, leg areas, and/or dashboard, may include the one or more proximity detectors 20*k*. For example, the vehicle user interface 16 may include proximity detectors 20*k*. The proximity detectors 20*k* may generate signals indicative of the patient entering the vehicle 10 and/or occupying the vehicle 10. Further the proximity detectors 20*k* may indicate the position of the patient and/or other occupants of the vehicle 10 in the vehicle. In an implementation, the proximity detectors 20*k* may provide signals indicative of a total number of occupants and seat positions of all of the occupants. The proximity detectors 20*k* may utilize, for example, RFID tag technology, low-power Bluetooth® technology, Near Field Communication, etc. As other examples, the proximity detectors 20*k* may include capacitive, infrared, ultrasonic, and/or optical sensors, etc. The proximity detectors 20*k* may include short range and/or long range sensors. In an implementation, the proximity detectors 20*k* may sense gestures of a vehicle occupant. For example, the gesture sensing may provide a signal to the vehicle 10 that the vehicle 10 includes a medical device, for example, the wearable medical device 100. The proximity detectors 20*k* may provide sensed information to the wearable medical device 100, for example, via the vehicle sensor monitor 40.

In an implementation, the vehicle sensor monitor 40 may detect the presence of the wearable medical device 100 on an occupant of the vehicle 10 based on signals received from the one or more vehicle sensors. Further, the vehicle sensor monitor 40 may determine whether the driver and/or one or more passengers are wearing the wearable medical device 100. For example, the wearable medical device 100 may provide a signal to the vehicle sensor monitor 40 indicative of the existence of the wearable medical device 100 in the vehicle. As another example, the camera 30 may be configured to detect the wearable medical device 100 via image analysis.

In an implementation, the vehicle 10 may be an autonomous vehicle, also referred to herein as a self-driving vehicle, and/or a vehicle that provides a capability of autonomous vehicle control but may also be controlled by a driver. The use of automation in the driving of road vehicles such as cars and trucks has increased as a result of advances in sensing technologies (e.g., object detection and location tracking), control algorithms, and data infrastructures. By combining various enabling technologies like adaptive cruise control (ACC), lane keeping assistance (LKA), electronic power assist steering (EPAS), adaptive front steering, parking assistance, antilock braking (ABS), traction control, electronic stability control (ESC), blind spot detection, GPS and map databases, vehicle to vehicle communication, and other, it becomes possible to operate a vehicle autonomously (i.e., with little or no intervention by a driver). The vehicle 10 may include an autonomous driving controller 50. In an implementation the autonomous driving controller 50 is configured to couple to and coordinate operation of a plurality of subsystems to obtain autonomous vehicle functioning.

Figure 1D:
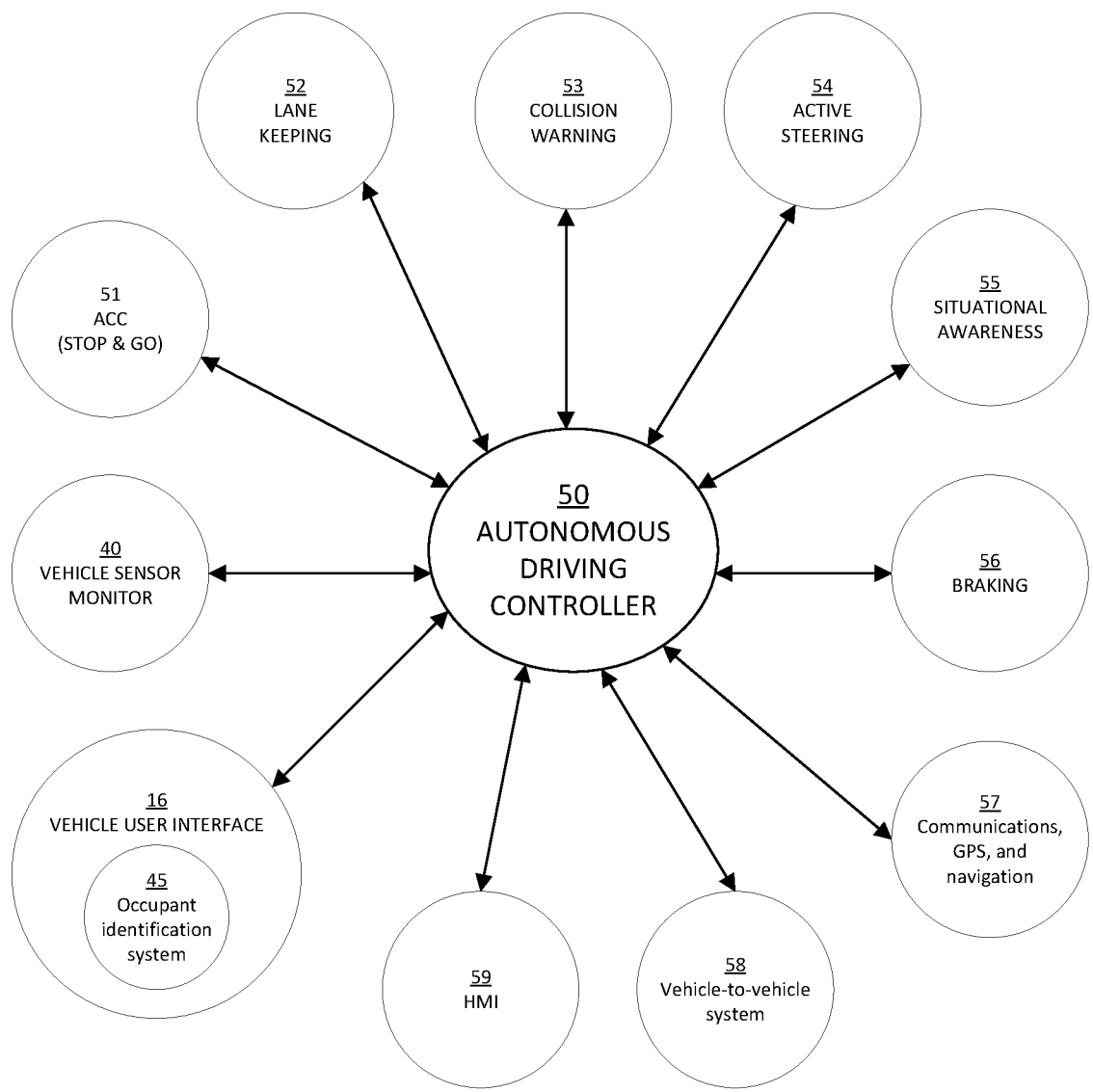
FIG. 1D is a schematic diagram of a plurality of subsystems coupled to and coordinated by an autonomous driving controller in accordance with embodiments of the present disclosure.

Referring to FIG. 1D, a schematic diagram of the plurality of subsystems coupled to and coordinated by the autonomous driving controller 50 is shown. An adaptive cruise control (ACC) module 51 may provide a "stop and go" function capable of controlling vehicle forward movement in response to both a leading vehicle and traffic control devices such as stop signs and traffic lights. ACC module 51 may be configured to couple to an engine or powertrain control unit (not shown) for accelerating and decelerating the vehicle 10. A lane keeping module 52 may provide the functionality of a lane departure warning system and/or a lane-keeping assistance system. A collision warning system 53 may include forward, side, and rearward looking radar sensors and/or cameras providing data to an object identification and tracking system as known in the art. The collision warning system 53 may work together with other remote sensing components in a situational awareness block 55 to identify fixed or moving obstacles or other hazards. An active steering subsystem 54 responds to commands from the autonomous driving controller 50 for changing a vehicle heading (e.g., to make turns or to follow a desired lane). Slowing or stopping of the vehicle is provided by a braking system 56 which may include anti-lock braking and/or stability control subsystems. A communications, global positioning system (GPS), and navigation unit 57 is coupled to autonomous driving controller 50 for providing communications capabilities to the vehicle (e.g., wireless communication over a cellular, computer, or other communications network) vehicle position, speed, and heading information. A map database is stored within the GPS and navigation unit 57 or is remotely accessed by GPS and navigation unit 57 (e.g., over a wireless data connection) for route planning and monitoring. In an implementation, the unit 57 is configured to notify EMS if the medical device controller 120 detects a medical event or a medical premonitory event. The notification may be automatic and/or may require user confirmation. The information provided in the notification may depend on the type of ME or medical premonitory event and may depend on user configurable preferences. The notification may include the location of the vehicle 10, the location of the wearable medical device in the vehicle 10, driving conditions of the vehicle (e.g., speed, lane, etc.), navigation settings of the vehicle, and/or patient information. In the event that the unit 57 contacts EMS, the unit 57 may automatically notify the medical device controller 120 so that the call to EMS may be logged and/or displayed on the medical device user interface 220. Other remote information may be accessed wirelessly using a vehicle-to-vehicle (V2V) system 58, for example.

In an implementation, the vehicle user interface 16 may include an occupant identification system 45. The occupant identification system 45 may be configured to identify one or more occupants of the vehicle 10. In one possible approach, the occupant identification system 45 may be configured to receive a key and identify one or more occupants based on one or more signals received from the key. Alternatively or additionally, the occupant identification system 45 may be configured to identify one or more occupants from signals received from the wearable medical device 100 (e.g., as disposed on an occupant of the vehicle) and/or from mobile devices located in or near the passenger compartment of the vehicle 10 and/or from images captured by, for example, a camera located in the passenger compartment. The wearable medical device 100 and/or the mobile devices may transmit vehicle occupant identification information to the occupant identification system 45. In an implementation, the vehicle occupant identification information may include medical care facility preferences, physician information for the patient, medical insurance information for the patient, and/or medical history information. For example, the medical history information may include current drug prescription, drug allergies, ongoing medical conditions, etc. The occupant identification system 45 may be configured to provide some or all of the occupant identification information to emergency medical services (EMS) (e.g., via wireless communication with a public safety answering point), to the vehicle user interface 16, and/or to an external mobile device associated with an emergency responder. In an implementation, the occupant identification system 45 may provide occupant information selectively based on a severity or predicted severity of the ME. In such an implementation, the patient may select patient information sharing preferences for the wearable medical device 100, for example, via the user interface pod 140 and/or the medical device user interface 220. In an implementation, the occupant identification system 45 may identify the occupant based on the identification code associated with the wearable medical device 100. For example, the camera 30 may provide the identification code information to the occupant identification system 45. In an implementation, the occupant identification system 45 may exchange and/or compare information with the medical device controller 120 (e.g. based on patient data storage 316) to identify and/or confirm the identity of the patient.

In an implementation, the vehicle sensor monitor 40 may be coupled to the autonomous driving controller 50. The vehicle sensor monitor 40 may provide vehicle occupant information to the autonomous driving controller 50. The vehicle occupant information may include the seat occupancy information and/or physiological information determined by the vehicle sensors 20a-20k and/or the camera 30. In a further implementation, the vehicle user interface 16 may be coupled to the autonomous driving controller 50. The vehicle user interface 16 may capture user input and provide the user input to the autonomous driving controller 50. Further the autonomous driving controller may provide driver feedback via the vehicle user interface 16.

Referring to FIG. 2A, an example of a wearable medical device 100 is shown. As illustrated in FIGS. 1B and 1C, one or more of the driver or the passenger and/or one or more passengers of the vehicle 10 may be wearing the wearable medical device 100. In some implementations, the wearable medical device 100 is an ambulatory device (e.g., a device that is capable of and designed for moving with the patient as the patient goes about his or her daily routine). The wearable medical device 100 may be an ambulatory defibrillator such as, for example, the LifeVest® wearable defibrillator available from ZOLL® Medical Corporation of Chelmsford, Mass. The wearable medical device 100 is configured for continuous, substantially continuous, long-term and/or extended patient use. The wearable medical device 100 is worn by or otherwise attached or connected to the patient. Continuous use may be use without substantial interruption for a predetermined period of time (e.g., hours, weeks, months, years). The wearable medical device 100 as described herein may be removed for a period of time before use, wear, attachment, and/or connection to the patient is resumed (e.g., to change batteries, to change the garment, and/or to take a shower), without departing from the scope of the examples described herein.

The wearable medical device 100 may include a user interface pod 140. The user interface pod 140 may include one or more input mechanisms (e.g., buttons, switches, touch pads, etc.) that the patient may interact with in order to respond to a treatment alert. In some examples, the wearable medical device 100 issues a treatment alert before providing a treatment shock, and if the patient does not respond to the treatment alert (e.g., by holding down one or more response buttons), the device may deliver the treatment shock to restore normal heart rhythm. The user interface pod 140 may further be configured to capture patient input indicating a use mode for the wearable medical device 100. For example, the patient may activate an input mechanism to indicate that the patient is entering a vehicle and the patient role in the vehicle (e.g., driver or passenger). The patient may further provide input to the user interface pod 140 indicative of a length of time that the patient expects to be in the vehicle and/or a driving distance.

The user interface pod 140 may control the vehicle navigation and/or be geo-location-aware via built in GPS capability and mapping tools such as Google Maps®, or have access to the navigational and geo-location capabilities in the vehicle 10 via the communications connection to the vehicle 10 (e.g., via the wireless communication device 20j). Decisions to re-route the vehicle may take place at an EMS dispatch facility and the commands and/or new destination may be transmitted back to the vehicle 10 based on, for example, hospital availability and appropriateness of medical care. Alternatively or additionally, the re-routing may be implemented in the wearable medical device 100 based on navigation and geo-location information. The interface pod may provide both audio, verbal and text prompting to the patient and any other passengers in the vehicle 10.

In case of detection of elevated risk and impending delivery of therapy, an audio and/or visual communications link may be established with medical personnel such as EMS dispatch, the patient's physician, or other qualified personnel. If after prompting, the patient is non-responsive, prompts may be delivered to ask if there is anyone else in the vehicle 10 that can respond or help.

The wearable medical device 100 includes a plurality of sensing electrodes 112 that can be disposed at various positions about the patient's body. The sensing electrodes 112 are configured to monitor one or more cardiopulmonary signals from the patient. As such, the sensing electrodes 112 monitor the cardiopulmonary function of the patient. For example, the cardiac information indicated by the cardiopulmonary signals may include, for example, but not limited to, heart rate, ECG data, and heart sounds data from an acoustic sensor. In an implementation, the wearable medical device 100 may include and/or may be coupled to additional physiological sensors 116 configured to sense and monitor other patient parameters, for example, but not limited to respiration rate, glucose levels, blood oxygen levels, lung fluids, lung sounds, and blood pressure. While FIG. 2A shows three sensing electrodes 112 as an example, the wearable medical device 100 may include fewer or additional sensing electrodes 112. The positions of the sensing electrodes 112 as shown in FIG. 2A are examples only and not limiting of the disclosure. The sensing electrodes 112 may be removably affixed to the garment 110 and may be rearrangeable based on particular needs of the patient and/or a particular mode of use.

The sensing electrodes 112 are electrically coupled to a medical device controller 120 through a connection pod 130. The connection pod 130 may include electronic circuitry and one or more sensors (e.g., a motion sensor, an accelerometer, etc.) configured to monitor patient activity.

In various implementations, one or more of the components of the wearable medical device 100 are affixed to a garment 110 that can be worn on the patient's torso. For example, as shown in FIG. 2A, the medical device controller 120 can be mounted on a belt worn by the patient. In an implementation, the sensing electrodes 112 and/or the connection pod 130 may be assembled and/or integrated into the garment 110. In a further implementation, the sensing electrodes 112 and/or the connection pod 130 may be affixed to the garment 110. Various components of the wearable medical device 100 may be packaged into modules that can be attached to or removed from the wearable medical device 100 as needed.

In some implementations, the wearable medical device 100 may include a plurality of therapy electrodes 114 that are electrically coupled to the medical device controller 120 through the connection pod 130. The therapy electrodes 114 are configured to deliver one or more therapeutic defibrillating shocks to the body of the patient in response to a signal from the medical device controller 120.

Alternatively, and as discussed in further detail below, the wearable medical device 100 may be a monitoring only device that omits the therapy delivery capabilities and associated components (e.g., the therapy electrodes 114). In some instances, the wearable medical device 100 may carry out its monitoring in periodic or aperiodic time intervals or times. For example, the monitoring during intervals or times may be triggered by a user action or another event. For example, one or more durations between the periodic or aperiodic intervals or times may be user-configurable.

In some examples, the sensing electrodes 112 and/or the therapy electrodes 114 may be disposable adhesive electrodes. In some implementations, the electrodes may be affixed to an electrode assembly (e.g., a patch), which can then be adhesively attached to the patient's skin. The sensing and/or therapy electrodes, and/or integrated electrodes can be attached to the patient's skin at particular locations as prescribed by a trained professional.

Figure 2C:
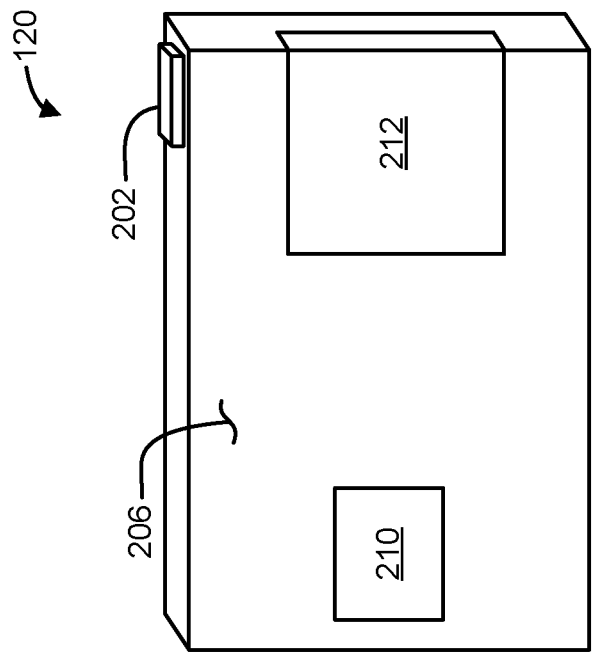
FIGS. 2B-2C are examples of a front view and a rear view, respectively, of the medical device controller of FIG. 2A.
Figure 2B:
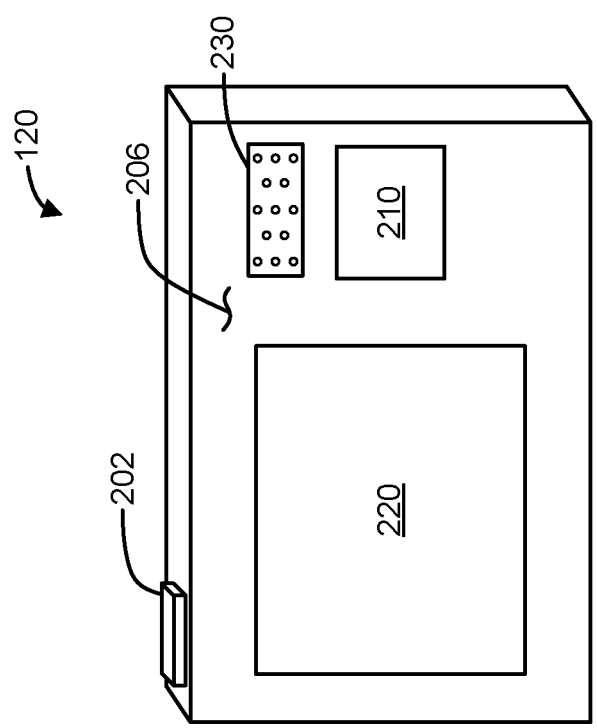

Referring to FIGS. 2B and 2C, examples of a front view and rear view, respectively, the medical device controller 120 of FIG. 2A are shown. The medical device controller 120 may be powered by a rechargeable battery 212. The rechargeable battery 212 may be removable from a housing 206 of the medical device controller 120 to enable a patient and/or caregiver to swap a depleted (or near depleted) battery 212 for a charged battery. In an implementation, the battery 212 is configured to couple to a vehicle charger cable and/or adapter and is configured to recharge in response to a connection to a vehicle battery. The medical device controller 120 may further include a port 202 to removably connect the sensing electrodes 112, the therapy electrodes 114, and/or other electrode patches and sensing devices, to the medical device controller 120.

The medical device controller 120 may include a medical device user interface 220. The patient and/or caregiver may interact with the medical device user interface 220 to control the medical device 100. The medical device user interface 220 may include a display configured to provide information to the patient, caregiver, and/or bystanders. The display may be a touch screen and/or may include visible indicators such as light emitting diodes (LED) and/or other interactive controls (e.g., buttons, switches, etc.) configured to capture user input. The medical device user interface 220 may capture input from the patient. For example, the medical device user interface 220 may provide a drop down menu or check list that allows the patient to select a particular symptom from a list. Options for patient systems may include one or more of: feeling a skipped beat, shortness of breath, light headedness, racing heart rate, fatigue, fainting, chest discomfort, weakness, dizziness, and/or giddiness. In addition, the patient may select a level of activity (e.g., light activity, moderate activity, rigorous activity, etc.) that he or she was performing when the symptom occurred. In an implementation, the patient may provide input to the medical device 100 via the vehicle user interface 16. For example, the patient may verbally provide symptom information and/or navigation information and may indicate another person that should be notified via the communications network 380.

Additionally, the medical device controller 120 includes response buttons 210 that the patient may interact with in order to communicate with the medical device 100. The medical device controller 120 may include an audio interface 230 that includes a speaker and/or a microphone. The audio interface 230 is configured to communicate information to and/or receive audio input from the patient and/or a bystander. For example, if the medical device controller 120 determines that the patient is experiencing cardiac arrhythmia, the speaker may issue an audible alarm to alert the patient and bystanders to the patient's medical condition.

In some examples, the medical device controller 120 may instruct the patient to press and hold one or both of the response buttons on the medical device controller 120 to indicate that the patient is conscious, thereby instructing the medical device controller 120 to withhold the delivery of one or more therapeutic defibrillating shocks. If the patient does not respond to an instruction from the medical device controller 120, the medical device 100 may determine that the patient is unconscious and proceed with the treatment sequence, culminating in the delivery of one or more defibrillating shocks to the body of the patient.

The vehicle operating mode may determine treatment parameters that control a therapy delivered by the wearable medical device 100. For example, such treatment parameters may control an intensity or a manner of therapy delivery. Further, the wearable medical device 100 may be configured to prohibit therapy delivery, even as medically indicated, based on the operating environment. For example, if the patient is the driver of a vehicle, the wearable medical device 100 may be configured to withhold or delay delivery of a defibrillation shock unless the vehicle is in an autonomous mode, stopped, out of traffic, etc. Additionally, the vehicle operating mode may effect changes in communication parameters (e.g., for controlling the transmission of data to and from the wearable medical device 100), alarm and notification parameters (e.g., for controlling the types, manner, and modes of alerting the patient, bystanders, and/or caregivers), and/or other device operating parameters (e.g., relating to battery circuit parameters, device self-monitoring and testing parameters, energy storage parameters, etc.). In an implementation, a volume of the audio and verbal prompts may be altered based on microphone road noise sensors or vehicle speed.

In an implementation, the one or more vehicle sensors (e.g., seat sensors and/or seat belt sensors) may provide signals indicative of the weight and/or height of the patient to the medical device controller 120. The medical device controller 120 may determine defibrillation shock energy based at least in part on the weight and/or height of the patient as determined from the vehicle sensors.

Figure 3:
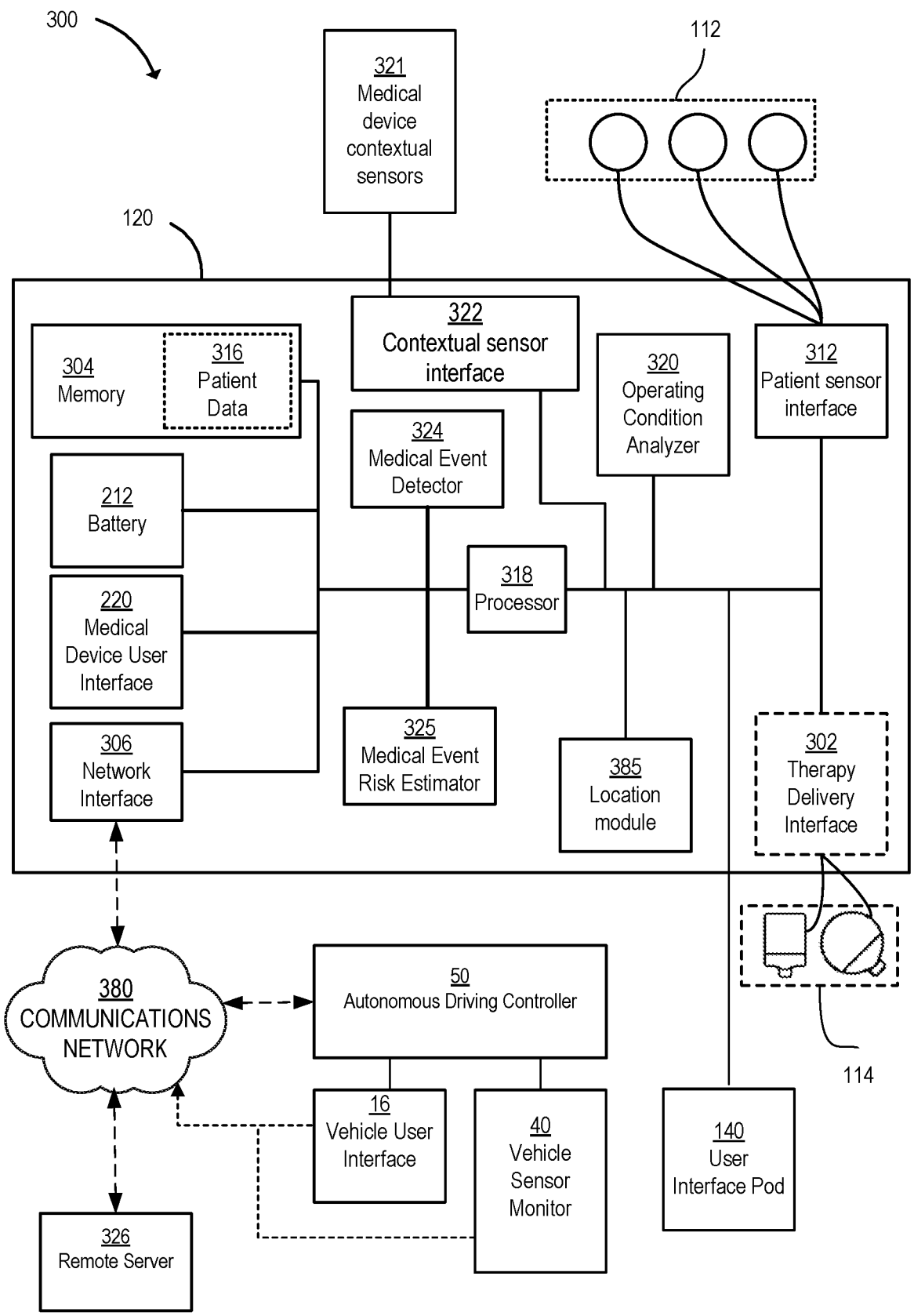
FIG. 3 is a schematic diagram of a medical device control system for a vehicle operating mode of the wearable medical device of FIG. 2A.

Referring to FIG. 3, a schematic diagram of an example of a medical device control system for a vehicle operating mode of the wearable medical device of FIG. 2A is shown. The medical device control system 300 includes the sensing electrodes 112, the therapy electrodes 114, and the medical device controller 120, for example as discussed above in reference to FIGS. 2A-2C. The medical device control system 300 further includes medical device contextual sensors 321, a vehicle user interface 16, a vehicle sensor monitor 40, and an autonomous driving controller 50.

The medical device controller 120 includes a processor 318, a memory 304 (which may include patient data storage 316), an operating condition analyzer 320, one or more medical device contextual sensors 321, a ME detector 324, a ME risk estimator 325, a patient sensor interface 312, an optional therapy delivery interface 302, an optional location module 385, a network interface 306, the medical device user interface 220, and the battery 212. The components 318, 304, 320, 321, 324, 325, 312, 302, 385, and 306 are communicatively coupled (directly and/or indirectly) to each other for bi-directional communication. Although shown as separate entities in FIG. 3, these components may be combined into one or more discrete components and/or may be part of the processor 318. The processor 318 and the memory 304 may include and/or be coupled to associated circuitry in order to perform the functions described herein.

The operating condition analyzer 320 may be configured to cause the medical device controller 120 to change the operating mode of the wearable medical device 100 in response to the use of the wearable medical device 100 in the vehicle 10. The operating condition analyzer 320 may receive signals from one or more of the medical device contextual sensors 321, the medical device user interface 220, the vehicle user interface 16, the vehicle sensor monitor 40, and/or the autonomous driving controller 50. The received signals may indicate the use of the wearable medical device 100 in the vehicle 10. Further, the received signals may indicate whether the patient is the driver of the vehicle 10 or a passenger in the vehicle 10. Based on these received signals, the operating condition analyzer 320 may transition the medical device controller 120 to the vehicle operating mode. The vehicle operating mode enables the wearable medical device 100 to communicate information to the vehicle 10 based on detected and/or predicted MEs. The communicated information may include notifications, alerts, messages, and/or commands. For example, the wearable medical device 100 may provide messages to the autonomous driving controller 50 that include recommended adjustments to operations of the vehicle based on the medical condition of the patient. Optionally, the vehicle operation mode may enable the wearable medical device 100 to adjust its own operations with regard to ME detection/prediction and/or therapy delivery based on the presence of the wearable medical device 100 in the vehicle 10.

The vehicle operating mode of the wearable medical device 100 may determine the timing of therapeutic events, a user response protocol required prior to delivery of therapy, a prohibition of the therapy even if recommended, and/or alerts, notifications, and/or warnings provided to the vehicle 10. One or more of the timing of therapeutic events, the user response protocol required prior to delivery of therapy, the prohibition of the therapy even if recommended, and/or the alerts, notifications, and/or warnings provided to the vehicle 10 may depend on whether a detected patient condition is a medical event (e.g., a current medical event) or a medical premonitory event (e.g., a future medical event). Additionally or alternatively, one or more of the timing of therapeutic events, the user response protocol required prior to delivery of therapy, the prohibition of the therapy even if recommended, and/or the alerts, notifications, and/or warnings provided to the vehicle 10 may depend on a particular time period associated with an event estimation of risk score for the medical premonitory event.

For example, for a non-autonomous vehicle, the operating condition analyzer 320 may cause the medical device user interface 220 to provide user feedback that may enhance the safety or outcome of a therapeutic shock delivery. The user feedback may include a request (e.g., as provided to the vehicle user interface 16) that the car be pulled out of traffic and/or stopped, a request that the car be driven to a hospital or other medical facility, or a request for a call or an automated call to emergency services. In an implementation, the request may indicate that these actions be immediate for the medical event or within the particular time period associated with the event estimation of risk score for the medical premonitory event for the medical premonitory event. The operating condition analyzer 320 may provide the user feedback prior to the delivery of therapy and may adjust a delay time interval prior to therapy in order to allow time for a user response to the feedback. The adjustment of the delay time interval may provide for a different delay time for the medical premonitory event than for the medical event based on the particular time period associated with an event estimation of risk score for the medical premonitory event.

For an autonomous vehicle, the operating condition analyzer 320 may communicate with the autonomous driving controller 50 to automatically adjust the operation of the vehicle 10 based on the medical condition of the patient. For example, the operating condition analyzer 320 may provide an instruction to the autonomous driving controller 50 to change a navigation route and take the vehicle 10 directly to a medical facility. The instruction may specify that these changes within a particular period of time from the issuance of the instruction depending on the event being the medical event or the medical premonitory event and/or depending on the particular time period associated with the event estimation of risk score for the medical premonitory event. Upon changing the navigation route of the vehicle 10, the operating condition analyzer 320 may provide an instruction to the autonomous driving controller 50 to activate a siren 60 or other emergency signaling mechanism on the vehicle 10. The operating condition analyzer 320 may require an indication from the autonomous driving controller 50 that the vehicle 10 is stopped in order to enable a delivery of a therapeutic shock. Alternatively or additionally, the operating condition analyzer 320 may require a confirmation from the autonomous driving controller 50 that the vehicle 10 is in an autonomous driving mode in order to enable the delivery of the therapeutic shock.

The operating condition analyzer 320 may be configured to provide a self-deactivation signal to the autonomous driving controller 50 if the ME detector 324 and/or the ME risk estimator 325 determines that a therapeutic shock is necessary. The autonomous driving controller 50 may execute a self-deactivation function configured to respond to the deactivation signal from the operating condition analyzer 320. The self-deactivation function may include a warning signal (e.g., an acoustic warning signal) may prompt the driver to pull the vehicle out of traffic (e.g., to the side of a road), brake, and turn off the engine and/or place the vehicle in park. If the driver does not respond to the warning signal within a reasonable time, the self-deactivation function is configured such that it initiates a controlled emergency braking of the vehicle to a standstill. The braking deceleration may be selected as a function of whether or not an automatic lane-keeping system is active such that the vehicle is brought to a standstill in a timely manner but the traffic following behind is not exposed to risk. In an implementation, the self-deactivation function may trigger an automatic turn-on of the warning light system of the vehicle. In various configurations, the lane keeping function of the vehicle may determine whether to automatically steer the car from the rightmost lane onto the shoulder during emergency braking or to limit the velocity of vehicle if the car is in a left hand lane and provide other warnings (e.g., flashing lights, sirens, etc.) prior to coming to a standstill on the roadway.

The ME detector 324 is configured to monitor physiological indicators from the patient (e.g., ECG signals and other cardiac parameters, respiratory parameters, etc.) and identify MEs (e.g., cardiac events) experienced by the patient based on received physiological indicators. The physiological indicators are provided to the ME detector 324 by the sensing electrodes 112 and/or from physiological sensor signals received from the vehicle sensor monitor 40. In an implementation, the ME detector 324 is configured to monitor signals from the one or more vehicle sensors to identify a ME experienced by the patient. For example, the one or more vehicle sensors may indicate that the patient is in a slumped position. Based in part on this indication, the ME detector 324 may detect syncope.

The ME risk estimator 325 is configured to monitor physiological indicators from the patient (e.g., ECG signals and other cardiac parameters, respiratory parameters, etc.) and detect and/or estimate medical premonitory events (e.g., elevated risk of cardiac events) for the patient based on received physiological indicators. Example methods and systems for medical premonitory event estimation are disclosed in issued U.S. Patent Application Publication No. 2016/0135706, entitled "Medical Premonitory Event Estimation," the contents of which are incorporated by reference in their entirety herein.

The ME risk estimator 325 may be configured to determine one or more event estimation of risk scores for the detected and/or estimated medical premonitory events. The event estimation of risk score for a particular time period is an estimate of a likelihood or probability of the patient experiencing a future medical event if treatment efforts are not taken or not successful and/or a determination that a cascade of events that will likely lead to a medical event without emergency response has already begun. Thus the event estimation of risk score may sometimes be referred to, an used interchangeably with, "event prediction" or an "event prediction score," though the term event estimation of risk is more comprehensive in that, unlike the weather, which cannot be altered substantially, one of the goals of using an event estimation of risk is to alter the potential course of a patient's status. An event estimation of risk enables a device or medical personnel to do more than just "carry an umbrella" to deal with events as they occur. An event estimation of risk may enable a device or medical personnel to prevent a medical event or reduce its effects. In addition to determining the event estimation of risk score, the ME risk estimator 325 may determine this score during multiple, different periods of time. Thus the ME risk estimator 325 may determine multiple different event estimation of risk scores associated with the potential of an adverse medical event for the patient with each of the different event estimation of risk scores being associated with a different time period. Each event estimation of risk score may indicate the probability of the adverse medical event occurring within a respective time period. The ME risk estimator 325 may therefore calculate different event estimation of risk scores for short term and long term likelihoods of an adverse medical event, such as the likelihood that the event will occur within one minute, ten minutes, one hour, three hours, one day, one week, one month, three months, etc. Providing these multiple event estimation of risk scores associated with different time periods may enable the operating condition analyzer 320 and/or the medical device controller 120 to provide time dependent information to the vehicle 10. Thus vehicle responses (e.g., actions taken by the autonomous driving controller 50 and/or information provided by the vehicle user interface 16) may be different for different particular time periods based on the likelihood of the adverse medical event happening within each particular time period. Thus the vehicle 10 may not be limited to just a choice of responding to a cardiac event or not responding to a cardiac event. Rather based on the event estimation of risk score, the medical device 100 described herein may enable the vehicle 10 to provide a more sophisticated response based on the timing associated with the calculated probabilities.

The various event estimation of risk scores for each of the time periods may be compared to stored event estimation of risk thresholds associated with the time periods to determine a plan of action or a response that varies based on the event estimation of risk scores for each of the estimated time periods. The risk score thresholds may be determined, for example, based on machine learning and/or statistical methods applied to estimated risk scores, realized patient outcomes, criticality of the predicted medical event, and/or confidence values associated with the estimated risk scores. Different time periods may be associated with different thresholds, and different medical events may be associated with different thresholds. For example, a threshold for applying defibrillation in response to a cardiac arrest for a more immediate time period may be different, e.g., and may be easier to satisfy, than a threshold for applying defibrillation in response to a cardiac arrest for a longer-term time period. A plurality of different event estimation of risk scores for a plurality of different medical events may be calculated for a single time period. For example, an event estimation of risk score for a cardiac arrest and an event estimation of risk score for a non-sustained ventricular tachycardia may be calculated for the same time period.

The physiological indicators are provided to the ME detector 324 by the sensing electrodes 112 and/or from physiological sensor signals received from the vehicle sensor monitor 40. As used herein, "premonitory" refers to an indication that something has a likelihood or probability of occurring, and a "medical premonitory event" refers to a ME that has a likelihood or probability of occurring for the monitored patient. The detection and estimation of medical premonitory events may thus be used as an early warning system to provide the patient, a bystander, and/or a medical professional time to prepare for the predicted ME. For example, the patient, a bystander, and/or a medical professional may prepare for a potentially adverse or fatal degradation in the medical condition of the patient, to potentially mitigate or avoid the adverse effects of the degradation, or even potentially completely avoid the degradation or event with timely, appropriate treatment.

The medical device 100 may provide driving control information to the vehicle 10. The driving control information may include instructions for one or more of the vehicle user interface 16 and the autonomous driving controller 50. The driving control information provided by the medical device 100 to the vehicle 10 may depend on an event estimation of risk score for a particular time period for the medical premonitory event and/or may depend on a type of medical premonitory event. For example, prompts and/or instructions to pull the vehicle out of traffic and/or otherwise modify planned travel, imminent travel, and/or travel already in progress may depend on the event estimation of risk score for the particular time period for the medical premonitory event. For example, the driver and/or passenger may provide a travel date and travel time (e.g., a time of departure) to one or more of the medical device user interface 220, the vehicle user interface 16, and/or the autonomous driving controller 50. The medical device 100 and/or the vehicle 10 (e.g., the operating condition analyzer 320 and/or the autonomous driving controller 50) may determine a course of action based on the event estimation of risk score for a particular time period subsequent to the travel time. The particular time period may be a short-term time period such as within minutes of the travel date and time (e.g., within 10 minutes, within 1-60 minutes, etc.) or within in hours of the travel date and time (e.g., within 1 hours, within three hours, within 1-24 hours, etc.). For example, if travel is initiated and/or already in progress and the event estimation of risk score exceeds a risk score threshold for a time period of less than 60 minutes (e.g., 1-60 minutes) from the detection of the premonitory medical event, then one or more of the vehicle user interface 16, the device controller 120, medical device user interface 220, and the autonomous driving controller 50 may generate an alarm and/or notification indicating that the vehicle should pull over to a side of the road and/or otherwise get out of traffic. In response, the patient, a passenger, and/or the autonomous driving controller 50 may change the vehicle location with regard to a thoroughfare based on the event estimation of risk score for the particular time period. For example, one or more of the medical device user interface 220 and the vehicle user interface 16 may provide a request that the car be pulled out of traffic and/or stopped, a request that the car be driven to a hospital or other medical facility, or a request for a call or an automated call to emergency services. As another example, the operating condition analyzer 320 may communicate with the autonomous driving controller 50 to automatically adjust the operation of the vehicle 10 based on the medical condition of the patient. For instance, the operating condition analyzer 320 may provide an instruction to the autonomous driving controller 50 to steer the vehicle 10 out of traffic and/or take the vehicle 10 directly to a medical facility. As a further example, the wearable medical device 100 may issue a command and/or a message to the autonomous driving controller 50 to take over driving (e.g., control steering, acceleration, and/or braking of the vehicle 10) in the autonomous or a semi-autonomous mode to safely guide the vehicle 10.

As another example, the driver and/or passenger may provide (e.g., input via a user input device) a trip itinerary to one or more of the medical device user interface 220, the vehicle user interface 16, and/or the autonomous driving controller 50. Thus the travel of the vehicle 10 may be programmed according to the trip itinerary. The trip itinerary may indicate and/or correspond to intervals of travel time associated with travel routes and/or destinations. For example, the trip itinerary may indicate one or more travel dates, travel destinations, travel routes, and/or times of departure and/or arrival. If the event estimation of risk score for a time period within the intervals of travel time exceeds the risk score threshold, then one or more vehicle user interface 16, the device controller 120, medical device user interface 220, and the autonomous driving controller 50 may generate an alarm and/or notification indicative of an actual change or a recommended change in the travel itinerary or a portion of the trip itinerary based on the event estimation of risk score for the particular time period. For example, the operating condition analyzer 320 may provide an instruction to the autonomous driving controller 50 to change a navigation route on the trip itinerary and take the vehicle 10 directly to a medical facility. As another example, the medical device 100 may provide an instruction for the vehicle user interface 16 to display the instructions and/or an associated alarm or warning for the driver and/or passenger to change at least a portion of the trip itinerary based on the event estimation of risk score. The portion of the trip itinerary may correspond to the particular time period for the high estimation of risk score. For example, the time period may be within 1-60 minutes of the detection of the medical premonitory event. As another example, the time period may be within 1-24 hours of the detection of the medical premonitory event. In response, the patient, a passenger, and/or the vehicle under autonomous control may change the travel itinerary. For example, the change may include a destination change, a route change that may shorten a travel time, for example, or may re-route the patient to a medical care facility. Other driving control information may include instructions to change the driver of the vehicle or to call 911. The driving control information may include an indication of the particular time period for which to alter driving conditions and/or the trip itinerary.

Non-limiting examples of MEs (e.g., as detected by the ME detector 324 and/or predicted by the ME risk estimator 325) include, for example, cardiac events such as a myocardial infarction or cardiac arrest, profound bradycardia due to acute decompensated heart failure, acute coronary syndrome, etc. Non-limiting examples of degradation in medical condition may include inception of a disease state, progression or worsening of a disease state, and/or an adverse ME, such as arrhythmia, heart attack, a subject suffering from traumatic injury that undergoes a potentially fatal, rapid loss in blood pressure due to hard-to-detect internal bleeding. Other possible MEs or degradations in the medical condition of a subject may be due to physical injury, diabetes, septic shock, seizure or epilepsy, for example.

Non-limiting examples of medical premonitory events (e.g., as detected by the medical event risk estimator 325) may include ectopic beats, runs of ectopic beats, ventricular tachycardia, bradycardias, and/or irregularities or abnormalities in P wave, QRS complex, T wave and U wave. Such events may be tangible events that are detectable by a trained clinician. Irregularities or abnormalities in electrical activity of the heart can include flattened T waves, inverted T waves, hyper-acute T waves or peaked T waves, beat-to-beat T wave variability, shortened QT interval, prolonged QT interval, wide QRS, prominent U waves, etc. Alternatively or additionally, medical premonitory events may include intermediate level events, such as the detection of clusters of events, accelerations of event rates, an increase in intensity or criticality of events, etc. Alternatively or additionally, medical premonitory events may include higher order events that may, for example, be defined in a multidimensional parameter space, e.g., the parameters comprising electrocardiogram ("ECG") data and/or other relevant physiologic parameters and/or patient demographics and other health history.

The sensing electrodes 112 may monitor the patient for indications of an indications of an oncoming cardiac event so that actions may be taken to reduce the probability of the occurrence of the cardiac event and/or mitigate harm to the patient due to the cardiac event. The medical event risk estimator 325 may determine an event estimation of an elevated risk of one or more cardiac events, including, for example cardiac arrest, ventricular tachycardia ("VT"), ventricular fibrillation ("VF"), pulseless electrical activity ("PEA"), asystole, etc. The elevated risk may correspond to a risk of a future ME that is higher than a baseline risk of the future ME. In A medical professional may prescribe the wearable medical device 100 to monitor the patient based on the patient having experienced a cardiac event in the past, being in recovery from cardiac or other surgery, and/or having indicated other signs of possible cardiac dysfunction, for example, an otherwise unexplained loss of consciousness, rapid heartbeat, or chest pain.

The medical device contextual sensors 321 may include one or more sensors disposed on the wearable medical device 100 and configured to detect the operating environment (e.g., the context) of the wearable medical device 100. For example, the medical device contextual sensors 321 may detect environmental parameters that indicate that the wearable medical device 100 is being used in the vehicle 10. These environmental parameters may include, but are not limited to, noise, vibration, acceleration, patient calendar information, etc. In an implementation, the wearable medical device 100 may detect use in the in vehicle 10 without receiving any signals from the vehicle 10. Thus the wearable medical device 100 may determine its environment use independently (e.g., without using information from vehicle sensors). In an implementation, the medical device contextual sensors 321 may access user calendar information or other personal information for the user to determine that the patient is in the vehicle 10. For example, user calendar information may indicate a commute to work or a driving vacation or other scheduled activity requiring vehicular transportation. For example, the patient may provide calendar or other information to the medical device user interface 220. As another example, the medical device controller 120 may be communicatively coupled to a mobile device or other computing device associated with the patient. The mobile device or other computing device may have stored calendar information and/or other personal information.

The medical device contextual sensors 321 may include one or more of motion sensors, resistive potentiometers, capacitive sensors, differential transformers, accelerometers, humidity sensors, pressure sensors, position sensors, force sensors, shock sensors, piezo sensors, strain gauges, optical sensors, moving-coil sensors, temperature sensors, imaging sensors, electro-optical sensors, sound sensors, microphones, ultrasonic sensors, radiation sensors, and flow sensors, among others. The contextual sensor interface 322 may provide the sensed signals from the medical device contextual sensors 321 and/or information based on the sensed signals to the processor 318, the ME detector 324, the ME risk estimator 325, and/or the operating condition analyzer 320. For example, based on parameters such as noise, acceleration, speed, or other contextual indicators, the medical device contextual sensors 321 may include vehicle occupancy sensors configured to provide signals indicative of the patient being in and/or operating the vehicle 10.

The processor 318 may execute processor-executable instructions stored in the memory 304 to control operations of one or more of the components of the medical device controller 120. The patient data storage 316 of the memory 304 may include patient identification information and patient medical information. The patient medical information may include, for example, but not limited to, patient medications, chronic, historic and/or potential medical conditions, physician information, medical specialist information, one or more preferred medical treatment locations, and patient characteristics (e.g., gender, height, weight, etc.). The patient sensor interface 312 is configured to couple to the sensing electrodes 112, and the therapy delivery interface 302 is configured to couple to the therapy electrodes 114. The patient sensor interface 312 and the therapy delivery interface 302 implement a variety of coupling and communication techniques for facilitating the exchange of data between the electrodes 112 and 114 and the medical device controller 120.

As discussed above, in an implementation, the wearable medical device 100 may be a monitoring-only device that omits the therapy delivery capabilities and associated components (e.g., the therapy electrodes 114). For such an implementation, the medical device controller 120 may exclude the therapy delivery interface 302 and/or may prohibit the functions of the therapy delivery interface 302 (e.g., via software, firmware, and/or hardware controls and/or settings). The monitoring-only device is configured for use by a patient who is at risk of developing cardiac problems, but who does not yet meet criteria to be outfitted with the wearable medical device that includes therapy electrodes (e.g., defibrillation electrodes). Thus, the monitoring-only device may be prescribed so that continuous and/or event-based data may be sent from the medical device controller 120 to a server (e.g., the remote server 326) via the communications network 380. A caregiver rescuer may access the data from the remote server 326 and determine whether the patient is experiencing or has experienced a cardiac problem. In some implementations, after determining that the patient is experiencing a cardiac problem, the caregiver may instruct the patient to begin wearing the wearable medical device 100 with therapy delivery capabilities (i.e., the wearable medical device 100 that that includes and provides for operation of the therapy delivery interface 302 and the therapy electrodes 114). The monitoring-only device may exclude the garment 110. In such an implementation, the medical device controller 120, the connection pod 130 and optionally the user interface pod 140 may be disposed on a belt or holster and may be coupled to the sensing electrodes 112 as disposed on the body of the patient.

The network interface 306 may enable communication of information between the medical device controller 120 and one or more other devices or entities over a communications network 380. The communications network 380 may be, for example, but not limited to, a local area network, a cellular network, and/or a computer network (e.g., an Internet Protocol network). The network interface 306 may provide Wi-Fi, Bluetooth®, satellite, and/or cellular communications capabilities. In an implementation, the network interface 306 may communicate with a server (e.g., a remote server 326). A caregiver may access the data from the remote server 326 to access information related to the patient.

In various implementations, the processor 318, the ME detector 324, the ME risk estimator 325, and/or the operating condition analyzer 320 may receive information from the vehicle user interface 16, the vehicle sensor monitor 40, and/or the autonomous driving controller 50 via the network interface 306. Alternatively or additionally, the processor 318, the ME detector 324, the ME risk estimator 325, and/or the operating condition analyzer 320 may receive information from the vehicle user interface 16, the vehicle sensor monitor 40, and/or the autonomous driving controller 50 via one or more wired connections between the wearable medical device 100 and the vehicle 10. For a non-autonomous vehicle, the vehicle user interface 16 and/or the vehicle sensor monitor 40 may communicate with the medical device controller 120. For the autonomous vehicle, the vehicle user interface 16 and/or the vehicle sensor monitor 40 may communicate with the medical device controller 120. Alternatively or additionally, for the autonomous vehicle, the vehicle user interface 16 and/or the vehicle sensor monitor 40 may communicate with the autonomous driving controller 50 and the autonomous driving controller 50 may provide a communications link to the medical device controller 120.

In some implementations, the medical device controller 120 includes the location module 385. The location module is configured to determine the geo-location of the wearable medical device 100. The location module 385 may provide one or more signals to the processor 318 that are indicative of a geo-location of the wearable medical device. The location module 385 may be configured to determine the geo-location of the wearable medical device 100 based one or more of a global positioning system (GPS) and/or cellular network system. The location module 385 may include a GPS module and/or other navigation module capable of determining that the wearable medical device 100 is in the vehicle 10. In an implementation, the wearable medical device 100 may determine that it is located in a vehicle based on a navigation route (e.g., based on a determination that the wearable medical device 100 is on a roadway) and/or motion parameters (e.g., velocity and acceleration) determined by the location module 385 based on changes in location. The processor 318 may provide navigation commands, recommendations, messages, notifications and/or other information to the vehicle 10 based on the one or more signals received from the location module 385 (e.g., signals indicative of the geo-location of the wearable medical device.). In an implementation, the wearable medical device 100 may enter the vehicle operating mode when the patient is determined to be moving in a vehicle based on the GPS data. In an implementation, the medical device controller 120 may measure audio information (e.g., via a microphone, for example, as included in the medical device user interface 220) and correlate the audio information with a particular context. In an implementation, the medical device controller 120 may provide information in multiple languages based on the location as determined by the location module 385.

The autonomous driving controller 50 may function in several modes in order to control the vehicle 10 in cooperation with instructions from the medical device controller 120. For example, the autonomous driving controller 50 may function in a set-up mode, an active drive mode, a safe shutdown mode, and an emergency response mode.

The set-up mode may specify a driving route and establish communications with the medical device controller 120. In an implementation, during the set-up mode, the vehicle sensor monitor 40 may detect the presence of the wearable medical device 100 on an occupant of the vehicle 10 based on signals received from the one or more vehicle sensors. Further, the vehicle sensor monitor 40 may determine whether the occupant of the vehicle 10 wearing the wearable medical device 100 is the driver or a passenger. In an implementation, more than one passenger may be wearing wearable medical devices. In such an implementation the vehicle sensor monitor 40 may determine one or more passenger positions in the vehicle 10 that are associated with wearable medical devices. For example, the medical device controller 120 may pair with or otherwise establish a communications link to the autonomous driving controller 50 via the network interface 306. During the set-up mode, the vehicle sensor monitor 40 may notify the medical device controller 120 and/or the autonomous driving controller 50 that the wearer of the wearable medical device 100 is in the vehicle 10. In response, the operating condition analyzer 320 of the medical device controller 120 may transition the medical device controller 120 to the vehicle operating mode. Further the vehicle sensor monitor 40 may identify the wearer as the driver or the passenger in the vehicle 10.

In an implementation, the operating condition analyzer 320 may self-determine that the wearable medical device 100 is in the vehicle based on one or more signals from the medical device contextual sensors 321 as described above. The operating condition analyzer 320 may provide information to the vehicle 10 (e.g., to the vehicle user interface 16 and/or the autonomous driving controller 50) indicative of the wearable medical device 100 being located in the vehicle 10. Further, the information provided by the operating condition analyzer 320 may be based on the location of the patient in the vehicle 10 (i.e., driver or passenger) and/or may be based on whether the medical device 100 detects the medical event or the medical premonitory event. Further the information may be based on an event estimation of risk score associated with the medical premonitory event for a particular time period.

In a manual control mode for the vehicle 10, the driver retains active control of some or all of the driving functions (e.g., steering, accelerating, and braking). If the driver wishes to utilize an autonomous driving function, then an activation command is generated using the vehicle user interface 16. In response to activation of the autonomous driving function, a transition is made to the set-up mode. In the set-up mode, the driver identifies a destination and/or a driving route to be followed by the autonomous driving function. The route may be automatically calculated by a navigation system based on the destination and pre-set routing criteria as known in the art. Once the destination and route are selected, the driver may issue a command via the user interface 16 to initiate autonomous driving along the route.

The active drive mode is used for performing autonomous steering, acceleration, and braking functions to navigate along the driving route. The safe shutdown mode is used for identifying and autonomously proceeding to an out-of-traffic stopping location. In an implementation, a signal from the medical device controller 120 indicative of a reduction in cardiac health and/or a recommendation for a therapeutic intervention (e.g., a delivery of a defibrillation shock) may trigger the safe shutdown mode. The safe shutdown mode may occur for the driver but not for the passenger.

The emergency response mode may autonomously perform an emergency intervention. The emergency intervention may include determining an emergency route to a medical assistance facility and performing autonomous steering, acceleration, and braking functions to navigate along the emergency route. In an implementation, the emergency intervention may include activating a siren and/or a warning light on a license plate or other vehicle component. Alternatively, the emergency intervention is comprised of identifying and autonomously proceeding to an out-of-traffic stopping location. The emergency intervention may include automatically transmitting a message to a public safety answering point. Once the vehicle stops at the desired re-routed destination or other safe location, the vehicle may return to the manual drive mode. The emergency response mode may further include providing feedback to a driver with regard to a detected health condition of the passenger, etc.

Figure 4:
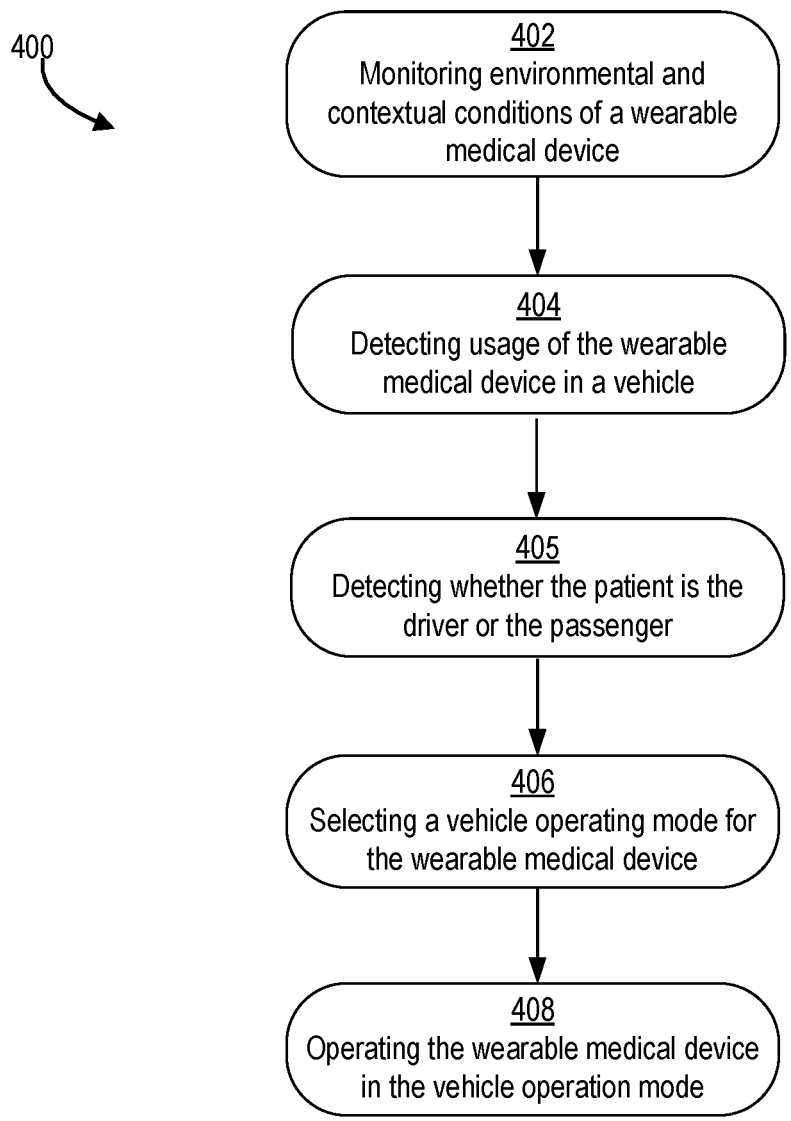
FIG. 4 is a block diagram of an example of a method for changing an operating mode for a wearable medical device in accordance with embodiments of the present disclosure.

Referring to FIG. 4, a method of changing an operating mode for a wearable medical device is shown. The method 400 is, however, an example only and not limiting. The method 400 can be altered, e.g., by having stages added, removed, rearranged, combined, and/or performed concurrently.

At stage 402, the method 400 includes monitoring the operating environment of the wearable medical device. For example, the operating condition analyzer 320 is configured to monitor signals from one or more sources (e.g., the medical device contextual sensors 321, the vehicle sensor monitor 40, and/or the autonomous driving controller 50) to determine if the operating environment of the wearable medical device 100 is the vehicle 10.

At stage 404, the method 400 includes detecting usage of the wearable medical device in a vehicle. For example, the operating condition analyzer 320 is configured to detect the usage of the wearable medical device 100 in the vehicle 10 based on the signals from one or more of the medical device contextual sensors 321, the vehicle sensor monitor 40, and/or the autonomous driving controller 50. Signals provided by the vehicle sensor monitor 40 and/or the medical device contextual sensors 321 may indicate that the patient is in the vehicle 10. Additionally, signals provided by the autonomous driving controller 50 may indicate that the vehicle 10 is turned on and prepared to travel or that vehicular travel has commenced. Alternatively or additionally, the patient using the medical device may indicate that she is in the vehicle with an input to a user interface device (e.g., the vehicle user interface 16, the medical device user interface 220 and/or the user interface pod 140). The operating condition analyzer 320 may receive a signal from the user interface device indicative of this input. A user other than the patient may provide this input to the user interface device. In some cases, such an input may simply be a confirmation of the detection provided by the operating condition analyzer 320, or may be a manual input independent from analysis performed by the operating condition analyzer 320 or associated contextual sensors 321.

At stage 405, the method 400 includes detecting whether the patient is the driver or the passenger. For example, one or more of the one or more vehicle sensors (e.g., 20a-20k) may detect the patient's seat position in the vehicle 10. In an implementation, the medical device contextual sensors 321 may detect the patient's seat position in the vehicle 10. The vehicle sensor monitor 40 may provide a signal from the one or more vehicle sensors indicative of the detected patient position to the autonomous driving controller 50 and/or the medical device controller 120.

At stage 406, the method 400 includes selecting a vehicle operating mode for the wearable medical device 100. For example, the operating condition analyzer 320 is configured to select the vehicle operating mode for the wearable medical device 100. In an implementation, the wearable medical device 100 is configured to operate in multiple operating modes include, but not limited to, a default operating mode, an activity operating mode, an exercise operating mode, a sleeping operating mode, a water operating mode, a shower operating mode, the vehicle operating mode, and combinations thereof. In such an implementation, the operating condition analyzer 320 is configured to select the vehicle operating mode from the multiple operating modes.

At stage 408, the method 400 includes operating the wearable medical device 100 in the vehicle operating mode. For example, the operating condition analyzer 320 is configured to switch the operating mode of the wearable medical device from an existing mode to the vehicle operating mode. In an implementation, switching the operating mode may include sending signals from the operating condition analyzer 320 to one or more of the processor 318, the ME detector 324, the ME risk estimator 325, the patient sensor interface 312, the therapy delivery interface 302, the medical device user interface 220, the network interface 306, and the user interface pod 140. The network interface 306 may provide signals indicative of the operating mode of the wearable medical device 100 to one or more of the remote server 326, the autonomous driving controller 50, and the vehicle sensor monitor 40. The autonomous driving controller 50 may provide a signal indicative of the operating mode of the wearable medical device 100 to the vehicle user interface 16. In response to the signal indicative of the operating mode of the wearable medical device 100, the various components receiving this signal may automatically adjust operational parameters according to the vehicle operating mode for the wearable medical device 100. In an implementation, the patient user may manually adjust one of more of wearable medical device settings for the vehicle operating mode. For example, the user may adjust settings via the medical device user interface 220 and/or the user interface pod 140.

In the vehicle operating mode, the medical device controller 120 may send driving control messages to the vehicle 10 (e.g., to the autonomous driving controller 50) via the network interface 306. The driving control messages may be based on the determined seat position of the patient in the vehicle 10 (i.e., whether the patient is the driver or the passenger).

In an implementation, when the wearable medical device 100 is in the vehicle operating mode, the operating condition analyzer 320 may continue to monitor the environmental and/or contextual conditions to determine if the wearable medical device 100 should exit the vehicle operation mode and switch to the default operating mode or a different specialized operating mode. For example, when the signals received from the vehicle sensor monitor 40 and/or the medical device contextual sensors 321 indicate that the patient is no longer in the vehicle 10, the wearable medical device 100 may exit the vehicle operating mode and return to a default operating mode. In some examples, the wearable medical device 100 may be configured to automatically switch to the default operating mode after a predetermined amount of time has elapsed. The amount of time that the wearable medical device 100 remains in a special operating mode may be configured by a user. For example, a user may preconfigure the wearable medical device 100 to exit the vehicle operating mode after a pre-determined amount of time. In an implementation, the pre-determined amount of time may correspond to a navigation estimate of a time of arrival at a destination. In an implementation, the patient or other user may be alerted or prompted by the wearable medical device 100 to provide input confirming that the wearable medical device 100 should exit the vehicle operating mode and return to the default operating mode. As noted above, the wearable medical device 100 may also switch to a different special operating mode from the vehicle operating mode.

In an implementation, the user may be prompted to confirm a mode change before the wearable medical device 100 effects the change to the vehicle operating mode. For example, the device may automatically enter the vehicle operating mode after a predetermined timeout period (e.g., 10-45 seconds, 1-2 minutes, or more) during which a user's response to such a prompt is not received. For example, the predetermined timeout period may be user configurable via a user interface (e.g., during initial setup and/or baselining and/or patient fitting).

In some examples, after the wearable medical device 100 enters the vehicle operating mode, the wearable medical device 100 may be configured to re-baseline the patient. As discussed below, a treatable condition may be determined based on changes in the heart axis information from a patient normal condition (e.g. baseline values, such as a baseline ECG recording). In this regard, the patient monitored by the wearable medical device 100 may be prompted to carry out a re-baselining process to prepare new ECG templates to be used when the wearable medical device 100 is in the vehicle operating mode. In some implementations, the re-baselining process may occur automatically in response to detecting the change in operating mode. During the re-baselining process, a baseline set of information relating to the patient may be captured as the new set of templates for detecting treatable conditions in the vehicle operating mode. In some examples, after the wearable medical device 100 exits the vehicle operating mode, the wearable medical device 100 may be configured to re-baseline the patient. Additional details concerning a method for baselining patients and determining treatable conditions based on the baselining are disclosed in the '669 patent described below.

Figure 5:
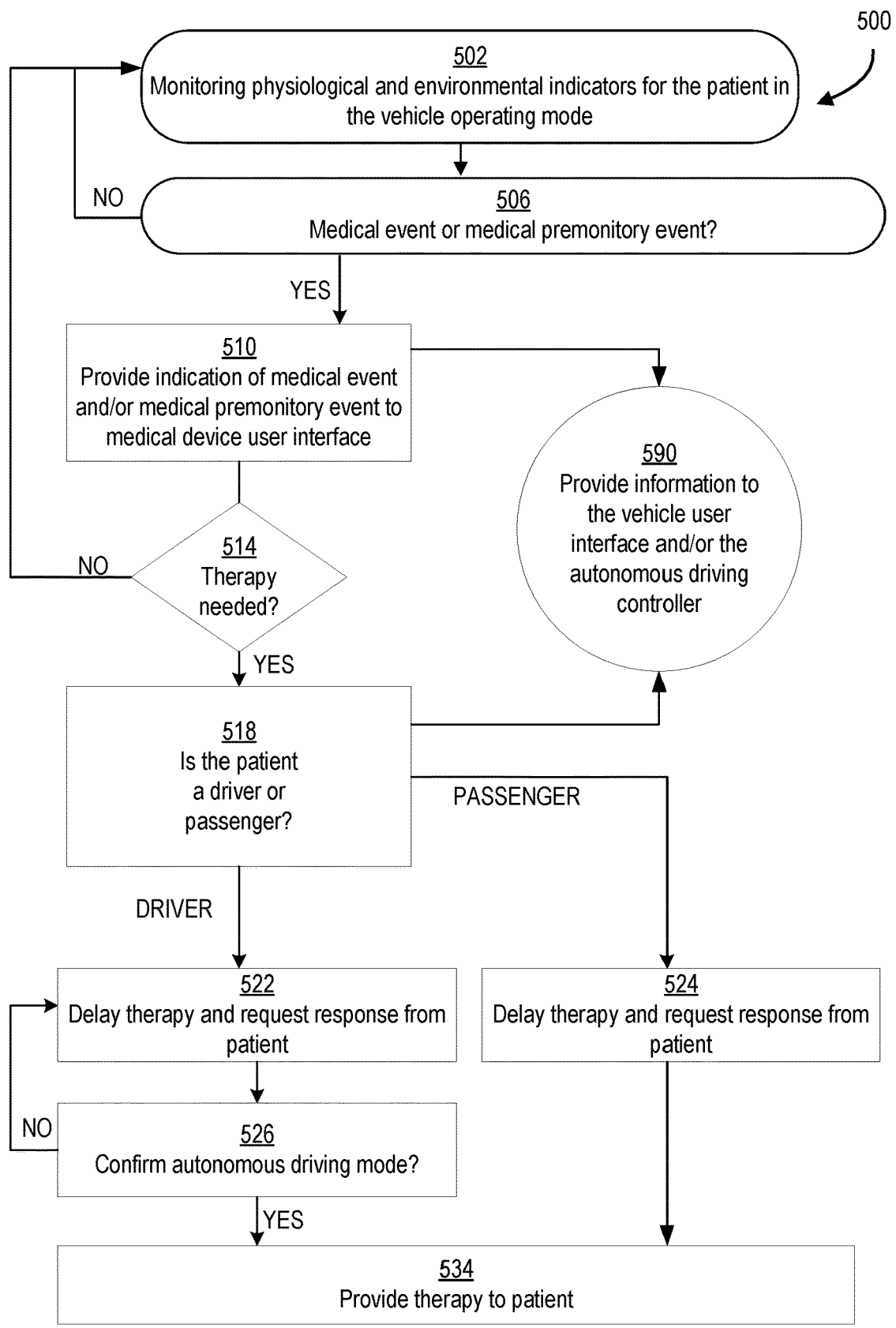
FIG. 5 is a block diagram of an example of a method of operating a wearable medical device in a vehicle operating mode in accordance with embodiments of the present disclosure.

Referring to FIG. 5, a method of operating a wearable medical device in a vehicle operating mode is shown. The method 500 is, however, an example only and not limiting. The method 500 can be altered, e.g., by having stages added, removed, rearranged, combined, and/or performed concurrently.

At stage 502, the method 500 includes monitoring physiological and environmental indicators for the patient. For example, the ME detector 324 and/or the ME risk estimator 325, may monitor signals from one or more of the sensing electrodes 112 (e.g., via the patient sensor interface 312), the medical device contextual sensors 321, the vehicle sensor monitor 40, and the autonomous driving controller 50. In an implementation, the ME detector 324 and/or the ME risk estimator 325, may further monitor user input to one or more of the user interface pod 140, the medical device user interface 220, and the vehicle user interface 16. In an implementation, the ME detector 324 may combine user input with sensor input in order to determine if the patient is experiencing a cardiac event. Alternatively or additionally, the ME risk estimator 325 may combine user input with sensor input in order to determine if the patient is at risk for a future cardiac event (e.g., within a predetermined future period of time, such as, within the next 1-10 minutes, 1 minute to 30 minutes, 1 minute to 1 hour, 1 minute to 3 hours). The ME detector 324 and/or the ME risk estimator 325 may monitor the patient indicators before, during, and after the selection of the vehicle operating mode.

At stage 506, the method 500 includes determining if patient is experiencing a ME or patient is at risk for a future ME (e.g., the medical premonitory event). For example, the ME detector 324 may determine that the monitored physiological indicators are indicative of a ME for the patient. As another example, the ME risk estimator 325 may determine that the monitored physiological indicators are indicative of a medical premonitory event for the patient.

If the ME detector 324 or the ME risk estimator 325 determines at the stage 506 that the patient is not experiencing the ME and is not at risk for the medical premonitory event, the method 500 returns to the stage 502 and continues to monitor the patient. If the ME detector 324 or the ME risk estimator 325 determines at the stage 506 that the patient is either experiencing the ME or is at risk for the medical premonitory event, then the method continues to the stage 510.

At the stage 510, the method 500 includes providing an indication of the ME and/or the medical premonitory event to the medical device user interface 220. For example, the processor 318 may provide one or more of an alarm signal and patient instructions to the medical device user interface 220 and/or the user interface pod 140. Details of therapy provided, timing of therapy, and instructions, prompts, alarms, and/or information provided to and/or from the vehicle user interface 16, the autonomous driving controller 50, and/or the medical device user interface 220 may depend on the detected event being the ME or the medical premonitory event since the ME is currently occurring and the medical premonitory event may occur at a time in the future. The response by the medical device 120 to the detected event also depends on the detected event being the ME or the medical premonitory event. Additionally, the relative risk of the medical premonitory event may determine the response by the medical device and/or the therapy details. For example, as discussed below, therapy may be delivered sooner for the detected ME than for the medical premonitory event. As another example, recommended changes to travel plans may be different for the detected ME than for the medical premonitory event. As a further example, the vehicle 10 may adjust transitions to the autonomous driving mode and/or adjust other automated controls of the driving depending on the detected event being the ME or the medical premonitory event.

In some implementations, the duration and/or number, and/or types of indications, and/or sequence of indications can be user configurable via the medical device user interface 220 and/or the user interface pod 140. For example, the patient and/or the caregiver may adjust the type, frequency, and/or volume of the alarms prior to use in the vehicle 10. The indication of the ME and/or the medical premonitory event may further include a description, medical response instructions, instructions to call emergency medical services, vehicular operational instructions (e.g., instructions to pull out of traffic, instructions to stop the vehicle, instructions to place the vehicle in an autonomous driving mode, etc.) and/or navigation instructions (e.g., listing of medical facilities, directions to the medical facilities). In an implementation, the navigation instructions may be based on location information from the location module 385. In such an implementation, the navigation instructions may include medical facilities in order of proximity to a current location of the patient and/or grouped by medical services offered (e.g., cardiac care, emergency care, hours of operation, etc.). These instructions may further depend on the detected event being the ME or the medical premonitory event.

At stage the 590, the method includes providing information to the vehicle user interface 16 and/or the autonomous driving controller 50 via the network interface 306 and the communications network 380. For example, the information may include the alarm signal, the patient instructions, the description, the medical response instructions, the instructions to call emergency medical services, the vehicular operational instructions, and/or the navigation instructions discussed above.

At stage 514, the method 500 includes determining if therapy (e.g., defibrillation therapy or pacing therapy) is needed immediately for an ongoing ME and/or will be needed in the future for the medical premonitory event. If therapy is not needed, then the method returns to the stage 502 and continues to monitor the patient. If therapy is and/or will be needed, the method 500 proceeds to the stage 518.

At stage 518, the method 500 determines if the patient is the driver or the passenger of the vehicle 10. For example, the operating condition analyzer 320 may determine whether the patient is the driver or the passenger. As described above, the operating condition analyzer 320 may receive signals indicative of the patient position in the vehicle from one or more of the medical device contextual sensors 321, the vehicle sensor monitor 40, the vehicle user interface 16, the autonomous driving controller 50, the user interface pod 140, and/or the medical device user interface 220. In an implementation, the signals indicative of the patient position are generated by one or more of the medical device contextual sensors 321 and/or one or more of the vehicle sensors 20*a*-20*k*. In an implementation, the patient may provide input to the vehicle user interface 16, the user interface pod 140 and/or the medical device user interface 220. The input may indicate that the patient is the passenger or the driver. In an implementation, the medical device controller 120 may prompt the patient for this input during transition to the vehicle operating mode.

In an implementation, the medical device controller 120 may provide the determined patient position information to the vehicle user interface 16 and/or the autonomous driving controller 50 at the stage 590. In this manner, the medical device controller 120 may notify the autonomous driving controller 50 that the driver and/or the passenger is outfitted with the wearable medical device 100. Further, the medical device controller 120 may provide therapy information to the vehicle user interface 16 and/or the autonomous driving controller 50 for therapy deemed necessary at the stage 514. The therapy information may indicate a treatment sequence. The treatment sequence may include a type of therapy (e.g., defibrillation, pacing, etc.), an expected timing of the therapy, an indication that the therapeutic treatment is about to be delivered, and/or a method by which the patient can stop the treatment from occurring. The treatment sequence may be selected, for example, by the medical device controller 120, based at least in part on the wearable medical device 100 being in the vehicle operating mode and based on the patient position in the vehicle as described below.

The information provided to the vehicle user interface 16 and/or the autonomous driving controller 50 may include one or more the following types of medical condition and response information: a current patient degree of impairment, a description of the ME and/or the medical premonitory event, an estimated time until the medical premonitory event, an estimated time until delivery of therapy, recommendations or commands for level of autonomous control, recommendations or commands for navigational destination, commands for level of autonomous control, and/or indications of patient position in the vehicle.

Examples of current patient degree of impairment include an indication that the patient is unconscious and an indication that the patient is likely unable to properly control the vehicle 10. Examples of the estimated time include an estimated quantity of time (e.g., an estimated time interval) until the medical premonitory event and a set of estimated risks at a series of time segments (e.g., as discussed in U.S. Pat. App. Pub. No. 2016/0135706). In the case of the ME, the event is already in process and thus the estimated time is zero.

Examples of the estimated time until delivery of therapy are as follows. In the case of the ME, there may be a shorter delay until the therapy is delivered as compared with the medical premonitory event. This gives the driver or the autonomous driving controller 50 time to transition the vehicle 10 to a safe condition, a condition that alerts surrounding vehicles and/or emergency responders, and/or a condition that facilitates rescue and/or emergency care (e.g., stopped, out of traffic, slowed down, activation of horn, siren, flashing lights, and/or hazard lights, call to emergency services, call to medical facility, unlocked doors, opened windows, navigation towards medical facility, etc.).

In an implementation, the vehicle 10 may be in a driver control mode (i.e., a manual control mode also referred to as a non-autonomous control mode) under control of the driver and patient. In the case of the medical premonitory event, the time frame until therapy may be 30 minutes and the risk of the event may below 20% within the next 30 minutes and the distance to the hospital may be less than 30 minutes. In this case, the autonomous driving controller 50 may communicate warning messages of an impending transition (e.g., in 10 seconds-5 minutes) to an autonomous control mode for the vehicle 10 audibly and/or visibly via the vehicle user interface 16. However, if the impending event and therapy are expected within 10 seconds, the autonomous driving controller 50 may immediately (e.g., in 1-10 seconds) take control of one or more of steering, acceleration and/or braking to prevent a vehicular accident at time of the ME or the therapy delivery.

In further implementations, the medical device controller 120 may send one or more of messages and/or notifications to one or more of the vehicle user interface 16 and/or the autonomous driving controller 50. For example, the messages may be driving control commands or recommendations, for example, steering, acceleration, and/or braking commands or recommendations. As another example, the driving control messages may be autonomous driving control commands or recommendations if the vehicle 10 is in and/or is capable of an autonomous driving mode. The autonomous driving control messages may include a command or recommendation to transition from a manual driving mode to the autonomous driving mode. As a further example, the driving control messages may include navigation instructions. The messages from the medical device controller 120 to the autonomous driving controller 50 may include one or more of the examples listed in Table 1 below. The autonomous driving controller 50 may communicate changes in routing or driving behavior of the vehicle 10 to the medical device controller 120 for logging and/or display on the medical device user interface 220. The medical device user interface 220 may audibly provide this information to the patient and/or a bystander.

In case of the detection of the ME and/or the medical premonitory event, prompts may be communicated from the wearable medical device 100 to the vehicle 10 and played over the built-in vehicle audio-visual systems such as car radio, video, heads-up windshield display, etc. These audio-visual systems may be components of and/or supplements to the vehicle user interface 16.

TABLE 1

| Type of Message/Notification | Message/Notification |
| --- | --- |
| Autonomous control | Full autonomous control required |
| | Park or stop vehicle |
| | Activate emergency lights |
| | Partial autonomous control required |
| | Control brakes |
| | Control steering |
| | Open windows |
| | Unlock doors |
| | Activate hazard lights and/or siren |
| | Patient is the driver |
| Information for occupants | Announce and/or display "Medical Emergency" |
| | Announce and/or display "Driver Medical Emergency" |
| | Announce and/or display "Passenger Medical Emergency" |
| | Announce and/or display transition to autonomous driving control |
| | Announce and/or display destination and/or navigation route changes |
| Navigation | Request to change a navigation destination due to a detected and/or predicted medical emergency |
| | Proceed to nearest emergency room |
| Communication | Transfer patient data to emergency medical services |
| | Connect to emergency medical services communication network |

In an implementation, the vehicle 10 may not be a self-driving car (i.e., may not include an autonomous driving controller). In such an implementation, the medical device controller 120 may provide the examples of messages above to a display and/or a speaker system associated with the vehicle 10 and/or with the wearable medical device 100. In such an implementation, the vehicle 10 may include an on-board diagnostics (OBD) II port. The medical device controller 120 may effect changes in the operation of the vehicle based on instructions and/or signals transmitted to the vehicle 10 via the OBD II port.

In response to receiving the medical condition and response information, the autonomous driving controller 50 may modify operations of the vehicle, send a confirmation of receipt to the medical device controller 120, display the information via the vehicle user interface 16, control the vehicle user interface 16 to request user input, and/or provide the medical device controller 120 with captured user input and/or vehicle operation information.

In response to receiving the medical condition and response information, the vehicle user interface 16 may send a confirmation of receipt to the medical device controller 120, display the information, request user input based on the received information, and/or provide the medical device controller 120 with captured user input and/or vehicle operation information. Further, the vehicle user interface 16 may provide instructions for the driver if the patient is in the passenger seat or instructions for the passenger(s) if the patient is in the driver's seat. The instructions may indicate that the patient is in a state of medical emergency. The instructions may include a description of the ME and/or medical premonitory event, medical response instructions, instructions to call emergency medical services, vehicular operational instructions (e.g., instructions to pull out of traffic, instructions to stop the vehicle, instructions to place the vehicle in an autonomous driving mode, etc.) and/or navigation instructions (e.g., listing of medical facilities, directions to the medical facilities). In an implementation, the navigation instructions may be based on location information from the location module 385. In such an implementation, the navigation instructions may include medical facilities in order of proximity to a current location of the patient and/or grouped by medical services offered (e.g., cardiac care, emergency care, hours of operation, etc.).

In an implementation, the medical device controller 120 may receive vehicle status information and/or navigational information from the vehicle 10 to determine what command or recommendation to send to the vehicle. For instance, the medical device controller 120 may receive the current vehicle location from the vehicle 10, the nearest hospital information from a service such as GOOGLE® Maps, ZOLL® EMS navigational software and/or EMS dispatch, then locate the nearest hospital, then send a recommendation or command to the vehicle 10 to go to that hospital.

The medical device controller 120 may also receive the vehicle autonomous control capabilities from the autonomous driving controller 50 at the time that communications are established between the wearable medical device 100 and the vehicle 10. For example, the vehicle 10 may have limited autonomous control capabilities that may provide for it to, for example, safely follow at a relative speed, stay in a lane, or pull over, but may not provide full-function navigational control. In this case, the commands or recommendations may be limited to having the vehicle safely pull over to the side of the road and may not include navigation to a hospital or other medical facility.

Referring again to the stage 518, if patient is determined to be the driver, the method proceeds to either stage 522 or stage 524 to request a response from the patient prior to a delivery of therapy at the stage 534. Stage 522 corresponds to the patient as the driver and stage 524 corresponds to the patient as the passenger.

Upon determining that therapy is needed (e.g., at the stage 514), the medical device controller 120 may provide an alarm. The medical device controller 120 may delay delivery of the therapeutic shock for a delay time interval so that, on perceiving the alarm, the patient may be able to instruct the medical device controller 120 to refrain from delivering the treatment shock. For example, the patient may instruct the medical device to refrain from applying a treatment shock if the patient is well and the medical device falsely identified the ME and/or medical premonitory event. The alarm may be an audible, visible, or haptic indication, or a combination thereof that the therapeutic shock is about to be delivered before it is actually delivered to the patient. The alarm may include one or more indications and/or a sequence of indications. The sequence may include several types of alarms (e.g., audible, visible, haptic) at varying volumes, brightness, vibration frequency etc. In an implementation, the medical device controller 120 may provide an indication of the alarm to the vehicle user interface 16.

The vehicle operating mode may correspond to a first delay time interval and a default operation mode may correspond to a second delay time interval. The delay time interval corresponds to the amount of time delay (e.g., the delay time interval) provided by the medical device controller 120 prior to therapy delivery. For example, in the default operating mode, the medical device controller 120 may give the patient a delay time interval of 30 seconds to stop a selected treatment from being applied. In an implementation, while operating in the vehicle operating mode, the medical device controller 120 may give the patient a longer or a shorter amount of time to stop a selected treatment from being applied.

The length of the delay time interval may depend on the patient position in the vehicle. Thus the delay time interval may be different for the driver than for the passenger. For example, for the driver, the amount of time may be longer than for the passenger. Alternatively, the response time may be shorter for the driver in order to treat the driver quickly so that the driver may re-gain control of the vehicle 10 or stop causing the reckless operation of the vehicle 10 due to the ME and/or medical premonitory event. For example, an alert sequence of the wearable medical device 100 in the default mode may include a tactile-only notification prior to an audible alarm. In the vehicle operating mode, the alert sequence may by-pass the tactile only notification. Alternatively or additionally, the medical device controller 120 may silence or mute audible information from the wearable medical device 100 and/or the vehicle 10 (e.g., audio entertainment or information) so that the patient can hear the alarm from the wearable medical device 100. Further, the medical device controller 120 may increase an alarm volume. In an implementation, the medical device controller 120 may increase a number of alarms in a sequence prior to delivery of therapy if the patient is the driver in order to provide time for the driver to get the car out of traffic or arrive at a medical facility.

As another example, the one or more settings may include at least one vehicle operation criterion for delivery of therapy. For example, the medical device controller 120 may receive one or more signals from the autonomous driving controller 50 (e.g., via the network interface 306). The medical device controller 120 may confirm the at least one vehicle operation criterion based on the one or more signals from the autonomous driving controller 50. In an implementation, for the driver, the medical device controller may not deliver the therapy without confirmation of an autonomous driving mode for the vehicle at stage 526. In an implementation, the time delay for a driver response may not commence until after the vehicle 10 has come to a stop. In an implementation, for the passenger, the wearable medical device 100 may automatically initiate the treatment sequence immediately or substantially immediately after the treatment sequence is selected.

In order to stop delivery of the therapeutic shock, the patient may interact with one or both of the response buttons 210 to cause the wearable medical device 100 to refrain from delivering the treatment. For example, the treatment may be a "false alarm," such as an unnecessary and/or erroneous treatment suggestion. In some examples, the patient may issue a verbal command (e.g., a spoken phrase such as "STOP TREATMENT" or "SUSPEND TREATMENT"). In some implementations, the wearable medical device 100 may include voice recognition capability to verify that the patient provided the command and not a bystander. Example methods and systems for using voice recognition to stop and/or suspend a treatment are disclosed in issued U.S. Pat. No. 8,369,944, entitled "Wearable Defibrillator with Audio Input/Output," the contents of which are incorporated by reference in their entirety herein. In an implementation, in the default operating mode, the patient may need to provide the input via the response buttons, but in the vehicle operating mode, the patient may provide the response via either the response buttons or as a verbal command. One or more other forms of input may be implemented in place of or in addition to either the response buttons or verbal commands. For example, patient motion information received from one or more of the vehicle sensor monitor 40, the medical device contextual sensors 321 and the sensing electrodes 112 may indicate that the patient is not unconscious. The patient motion information can be combined with other forms of input to confirm the input and stop and/or suspend treatment. In an implementation, the amount of time for a response to an alarm to stop and/or suspend treatment is user-configurable. For example, the amount of time may be set by the patient or another entity (e.g., a caregiver). In some implementations, the amount of time can be determined based on information stored in a database (e.g., a hospital database). In some implementations, receipt of an input only temporarily stops the therapy from being delivered to the patient, e.g., rather than ending the treatment sequence altogether. For example, receipt of the input can stop the therapy from being delivered, but can cause the ME detector 324 to compare input received from the monitoring component to one or more detection parameters and determine, based on the comparison, whether additional therapy (e.g., additional to the declined therapy) is needed.

For the patient determined to be the driver, the method proceeds from stage 522 to stage 526 prior to the therapy delivery at stage 534. For the patient determined to be the passenger at stage 518, the method proceeds from the stage 524 to the stage 534.

At stage 526, the medical device controller 120 may request confirmation from the autonomous driving controller 50 that the vehicle 10 is in an autonomous driving mode. In an implementation, a passenger may provide input to the vehicle user interface 16 to confirm that the vehicle 10 is in the autonomous driving mode. If the vehicle 10 is confirmed to be in the autonomous driving mode, the method 500 may proceed to stage 534 to provide the therapy to the driver. If the vehicle is not confirmed to be in the autonomous driving mode, the method 500 may return to the stage 522 and continue to delay therapy. In an implementation, the medical device controller 120 may request additional vehicle information from the autonomous driving controller 50. For example, the medical device controller 120 may request vehicle status information (e.g., lane position, speed, distance from medical facility, distance from home, indication of a stopped vehicle). In an implementation, the medical device controller 120 may delay therapy delivery until the autonomous driving controller 50 confirms that the vehicle is stopped and/or out of traffic.

At stage 534, the medical device controller 120 may provide the therapy to the patient. For example, the autonomous driving controller 50 may provide a confirmation to the medical device controller 120 that the vehicle 10 is in the autonomous driving mode. In response to this confirmation, the medical device controller 120 may provide therapy to the driver. As another example, in the absence of a stop therapy request from the passenger, the medical device controller 120 may provide the therapy to the passenger.

After the therapy is delivered, the ME detector 324 may compare input received from the monitoring component to one or more detection parameters. For example, input received from the monitoring component can be compared to the same detection parameters described above with reference to the stage 506 for determining whether the patient is experiencing a cardiac condition. In some implementations, the input received from the monitoring component can be compared to one or more other detection parameters. Based on the comparison, the ME detector 324 may determine whether additional therapy is necessary. For example, if the input received from the monitoring component indicates that the patient is experiencing normal heart function, the treatment sequence ends. On the other hand, if the input received from the monitoring component indicates that the detected cardiac condition persists (or, e.g., that a different cardiac condition exists), the ME detector 324 may determine that additional therapy is necessary and again provide an indication that a therapy is about to be delivered to the patient.

In some implementations, the wearable medical device 100 may be configured to automatically exit the special operating mode and return to the default operating mode after an initial treatment has been delivered. In some implementations, the wearable medical device 100 can cause a vehicle emergency communication system to automatically place an emergency phone (e.g., via OnStar®, 911, or other emergency dispatch, to alert emergency resources that a treatment has been delivered. As such, when the wearable medical device 100 switches to the default operating mode, the monitoring and/or treatment parameters can be appropriately adjusted for subsequent therapies. In some examples, the wearable medical device 100 can be configured to exit the special operating mode after the treatment sequence is completed and no further shocks are needed for the patient (e.g., after restoration of normal rhythm). In some implementations, the wearable medical device 100 can be configured to exit the special operating mode only after the entire treatment sequence is completed.

Cardiac Monitoring and Analysis and Noise Detection

As discussed above, the wearable medical device 100 is configured to monitor physiological information for the patient and analyze this information to detect MEs including, for example, cardiac events. Determining that the patient is experiencing a cardiac event may include a verifying that the patient's cardiopulmonary signals are in fact indicative of a cardiac condition. In some implementations, a cardiac condition may be erroneously identified due to the presence of noise in the cardiac signal (e.g., due to an electrode being partially removed from the patient, due to artifacts in the ECG signal due to vehicle motion, etc.). The wearable medical device 100 may analyze a portion of the patient's cardiac signal (e.g., a 20 second ECG portion) and determine whether the cardiac signal represents a noise artifact. The determination may be made according to a machine learning classifier based approach. In some implementations, the cardiac signal is assigned a score, and the score is compared to one or more predetermined cardiac event thresholds. Each cardiac event threshold may correspond to a particular type of cardiac event. For example, one threshold may correspond to a ventricular tachycardia (VT) condition, and another threshold may correspond to a ventricular fibrillation (VF) condition.

In some implementations, if the wearable medical device 100 initially determines that the patient may be experiencing a cardiac condition but subsequently determines that the supposed cardiac condition is due to a noise artifact in the cardiac signal, the ME detector 324 may be configured to modify the treatment sequence. For example, in some implementations, if a noise artifact is detected in the cardiac signal, the ME detector 324 may suspend the treatment sequence methodology for a period of time and refrain from providing any indication to the patient. This is sometimes referred to as a silent noise state, which can provide the ME detector 324 an opportunity to resolve the erroneous cardiac condition without user interaction. The length of the suspension may be based at least in part on the particular cardiac condition that is supposedly being detected and the operating mode of the device. For example, if the device is in the vehicle operating mode, then the length of suspension may be longer than the length of suspension in a default operating mode.

Following the treatment methodology suspension, if the cardiac event detector is unable to resolve the erroneous cardiac condition, the wearable medical device 100 may provide an indication that a therapy is about to be delivered. This is sometimes referred to as the noise alarm state, during which the treatment sequence methodology continues to run. If the patient provides an input, the wearable medical device 100 may extend the length of the noise alarm state for a period of time. The extended length of time may be based at least in part on the particular cardiac condition that is supposedly being detected. In some implementations, the patient can provide an indefinite number of inputs to indefinitely extend the noise alarm state.

As an example, the ME detector 324 can employ a spectral analyzer that uses fast Fourier transform (FFT), or other techniques, to measure and evaluate the respective SS and FB ECG input signal frequency components.

As a further example, the ME detector 324 and/or another component of the medical device controller 120 may include an axis analyzer to derive a signal representation of the electrical axis of the heart of a patient from whom ECG signals are received. Changes in the signal representation of the electrical axis of the heart can be evaluated to determine whether a treatable condition exists (e.g., the patient is experiencing a cardiac condition). For example, the signal representation can include a magnitude component and a phase component. In some examples, the phase component can indicate a zero-crossing indication. In some implementations, the axis analyzer can use a complex matched filter to analyze the ECG signals.

In some examples, the ME detector 324 can access patient baseline information in the form of templates (e.g., which may be stored in the patient data storage 316 of the memory 304 as patient data) that can assist the ME detector 324 in identifying cardiac events experienced by the particular patient, as described above. In an implementation, in response user input from the patient (e.g., as provided to the medical device user interface 220), the ME detector 324 can cause a portion of patient physiological information (e.g., in the form of a cardiac signal) to be captured for a length of time that is based on a time at which the symptom was experienced. For example, the ME detector 324 can cause a portion of an ECG signal of the patient to be captured. The portion of the ECG signal is sometimes referred to herein as an ECG strip. In some implementations, the wearable medical device 100 can continuously record ECG data while simultaneously identifying and recording one or more ECG strips relating to one or more events of interest (e.g., patient-reported symptoms, events detected by the ME detector 324, etc.). As such, if a caregiver wishes to view ECG data for a period of time prior to or after the recorded ECG strip relating to an event of interest, such data is available for review from the continuously-recorded ECG data. A treatable condition may be determined based on changes in the heart axis information from a patient normal condition (e.g. baseline values, such as a baseline ECG recording).

In this regard, the patient monitored by the medical device may undergo an initial baselining process. During the baselining process, a baseline set of information relating to the patient is captured. For example, a baseline ECG recording may be obtained. The baseline ECG may have a length of approximately 30 seconds to one minute. The baseline ECG values are fed into the analyzer in the form of filter coefficient values corresponding to the filters used in the analyzer. In particular, one or more specific comparisons of an incidence of zero phase crossing with periods of peaks of the magnitude component of the heart axis representation can be used to indicate the treatable condition. When the axis analyzer determines that a treatable condition exists (e.g., the patient is experiencing a cardiac condition), the axis analyzer can set a flag to indicate the condition. Additional details concerning a method for determining treatable conditions are disclosed in U.S. Pat. No. 5,944,669 (the "'669 patent") entitled "Apparatus and Method for Sensing Cardiac Function," the contents of which are incorporated by reference herein in its entirety.

In a default operating mode, once the baseline filter coefficients values are input to the axis analyzer, the axis analyzer continuously monitors the phase component for zero crossing conditions and when detected, the axis analyzer checks the magnitude component to determine whether the magnitude component is also above a magnitude threshold value. For example, the magnitude threshold value may be automatically calculated based on a prior history of the signal. Because amplitudes can vary according to a quality of the signal, the magnitude threshold value is allowed to vary within a preset of programmable range of values. In an example, the magnitude threshold value can be set to less than 90% of a previously detected peak level of the magnitude component.

In some examples, a sensitivity of the axis analyzer can be increased or decreased to reduce a number of false positives due to patient movements and/or activities and/or vehicle motion. For example, changes to the sensitivity can be made by changing corresponding parameters of the axis analyzer (e.g., changing phase detection and/or magnitude threshold parameters) dynamically in response to the patient movements and/or activities and/or the vehicle motion. Patient movement and/or activity can be detected through one or more patient movement sensors (e.g., accelerometers, gyroscopes, tilt sensors, etc. configured to detect patient movement). In an implementation, the medical device contextual sensors 321 may include the patient movement sensors. As another example, a heart sounds sensor (e.g., which can be included in the wearable medical device) may detect increased heart sounds activity indicating that the patient is performing an activity. The sensor data can be correlated with data from other sources to confirm that the patient is performing an activity and provide information related to the activity. With regard to vehicle motion, in an implementation, vehicle motion may be detected based on a signal from the vehicle motion sensor 20a and/or other signals received at the medical device controller 120 from one or more of the vehicle sensor monitor 40 and the autonomous driving controller 50. In some implementations, one or more parameters of the axis analyzer can be adjusted in a predetermined relationship with the input from the one or more sensors. A variety of other ways to control the settings of the device may be employed including, for example, machine learning and statistical techniques, among others.

In some examples, to achieve decreased sensitivity (e.g., where an intensity of signal noise or patient movement increases), it may be desirable to relax the requirements for declaring a match with baseline values. For example, the ME detector 324 may allow for more matching with one or more baseline values (e.g., to increase matching the received ECG signal with the baseline ECG recording). To allow for more frequent matching with baseline values, one or more phase detection parameters can be changed. For example, a zero crossing range can be increased from a default range such that the zero crossing condition detection rate is generally higher than the zero crossing condition detection rate in the default operating mode. In some examples, the magnitude threshold parameters can be changed. For example, the magnitude threshold value can be allowed to vary within a greater programmable range of values. For example, the magnitude threshold value can be set to 70-80% of a previously detected peak level of the magnitude component.

In some examples, it may be desirable to increase a sensitivity of the axis analyzer (e.g., by decreasing a zero crossing range from a default range such that the zero crossing condition detection rate is generally lower than the zero crossing condition detection rate in the default operating mode. For example, the magnitude threshold value can be configured to vary within a lesser range of values (e.g., 95% of the previously detected peak level of magnitude component).

In an implementation, the medical device controller 120 can be configured to automatically change a method of calculating one or more patient metrics. For example, as described in the '669 patent, in a default operating mode, a heart rate detector may be employed to determine whether the patient's heart rate is elevated. For example, a QRS detector can analyze signals from front-to-back (FB) electrodes and side-to-side (SS) electrodes and calculate FB and SS rates. These rates can be combined with an axis rate as determined by the axis analyzer and fed into a rate analyzer to provide final heart rate information. In a default operating mode, the heart rate can be calculated by averaging a rate obtained over a default number of beats (e.g., five beats). The ME detector 324 may adjust the calculation of the patient metrics, for example, to account for the patient being in the vehicle 10 (e.g., vehicle motion, driving induced stress, etc.). For example, the device may use eight, ten, or more beats to calculate the heart rate and thus be able to ride through noisy signals and/or events that may be encountered during certain operating conditions. In some implementations, such as instances involving certain other special operating conditions, it may be desirable to reduce a number of beats used to less than what is used in the default operating mode.

The operational sensing, monitoring, and/or detection parameters can include heart rate parameters. For example, while operating under certain operating conditions, heart rate thresholds may be changed in accordance with one or more principles as described herein. As background, if the patient's heart rate is sustained in an elevated zone as determined based on predetermined rate thresholds, then the patient may be experiencing a VT or VF event (e.g., assuming other detection parameters are also met as described above). For example, the predetermined rate thresholds can be input to the device via a user interface module during initial setup for the device. For instance, the predetermined rate thresholds may be set to a default value (e.g., 150 beats per minute for a VT type event, and 200 beats per minute for a VF type event). The default value may be adjusted to a new value (e.g., 160 beats per minute for a VT type event, and 210 beats per minute for a VF type event) via a user interface module.

In some implementations, while operating under certain operating conditions, the predetermined rate thresholds may be increased or decreased as appropriate depending on changes in the underlying operating conditions. For example, the vehicle driver exhibit different cardiopulmonary signals than the vehicle passenger. For instance, if the patient is driving the vehicle and possibly experiencing physiological stress, then the predetermined rate threshold may be configured to increase or decrease by a predetermined amount as compared to the default operating mode. For example, the physiological stress may be determined, for example, based on one or more of physiological indicators (e.g., ECG, heart rate, blood pressure, etc.) and roadway condition information (e.g., high speed, heavy traffic, highway travel, ice, snow, rain, or other weather, frequent lane changes, etc.). The ME detector 324 may receive roadway condition information from the autonomous driving controller 50. For the sedentary passenger, however, the ME detector 324 may implement a lessened threshold for detecting whether a cardiac condition exists, thereby having the effect of increasing the sensitivity of the wearable medical device 100. In an implementation, the vehicle sensor monitor 40 may provide patient activity information to the operating condition analyzer 320. The operating condition analyzer 320 may be configured to adjust thresholds based on the patient activity information from the vehicle sensor monitor 40.

In an implementation, the ME detector 324 may detect that the passenger is sleeping and the ME detector 324 may be configured to initiate its ability to detect sleep apnea in the patient. Indicators of sleep apnea may be related to transthoracic impedance, respiration rate, heart rate, certain pulmonary and/or heart sounds, and pulse oximetry, among others. The wearable medical device 100 can include one or more sensors configured to monitor one or more of these indicators to determine whether the patient is experiencing sleep apnea. In some implementations, the wearable medical device 100 is configured to alert the patient (e.g., with an audible and/or haptic alarm) if sleep apnea is detected. In some implementation, the detection of sleep apnea may indicate that the patient is experiencing a cardiac condition. Thus, in some implementations, a patient who is experiencing symptoms of sleep apnea, but who is not exhibiting other specific signs of a cardiac condition, may be treated as potentially experiencing a cardiac condition. In some implementations, the wearable medical device 100 may be configured to proceed with selecting a treatment sequence based on characteristics of the sleep apnea.

When the wearable medical device 100 is used in the vehicle 10, the vibration and other motion of the vehicle 10 may induce ECG artifacts. For example, the cardiopulmonary signals may be affected by motion of the vehicle and/or vibrations of the patient while in the vehicle. In an implementation, the wearable medical device 100 may incorporate signal processing filters and/or other algorithms to remove signal components due to vehicle motion and/or vibration from the ECG signal.

The ME detector 324 may adjust its sensitivity by changing one or more health metric thresholds (e.g., an ECG score). In some examples, the ME detector 324 may reduce its sensitivity by increasing an amount of detection time the device gives its noise algorithm to determine whether an identified event is a treatable VT/VF event. The reduced sensitivity can account for potentially inaccurate ECG signals. For example, if the value meets or transgresses the modified thresholds or if the device persists in declaring a treatable VT/VF event after an extended detection time, the medical device may determine that the patient may be experiencing a cardiac condition.

In some implementations, after the axis analyzer has detected a cardiac condition, the ME detector 324 can execute a noise detection function to confirm the condition. The noise detection function may verify the detected condition to distinguish a treatable cardiac condition from inappropriate sensing of, for example, a VT/VF condition due to noise caused by lead malfunction, electromagnetic interference, patient movement, etc. For example, the noise detection function can analyze a transformed version of the patient's ECG signal, such as a frequency domain representation of the signal, extract a value representing at least one feature of the transformed ECG signal, and determine an ECG score based on the at least one feature of the transformed ECG signal. The noise detection function can further compare the transformed ECG signal to a threshold. For example, the transformed ECG signal may be a presentation of a power distribution of the signal over a range of frequencies, which the noise detection function can calculate from, for example, a frequency domain representation of the ECG signal. For example, the transformed ECG signal can be a power spectral density (PSD) signal, which describes how the power of the ECG signal is distributed over different frequencies. The noise detection function may generate the PSD by performing fast Fourier transform (FFT) operations on the time domain ECG signal, or the noise detection function may employ other discrete Fourier transform (DFT) techniques to generate the PSD.

A PSD of an ECG signal demonstrating VT/VF typically has distinct features. For example, the PSD of an ECG signal demonstrating VT/VF may have several distinct dominant spectral bands. A normal sinus rhythm may have a dominant spectral band at less than 2.5 Hz. The frequency of VT/VF is typically greater than 2.5 Hz. The dominant spectral band is the band of frequencies that correspond to a maximum value of the PSD. A PSD with multiple dominant spectral bands has more than one band of frequencies in which the power of the ECG signal is significant. The information content in the PSD of the ECG signal that is in VT/VF is spread over more frequencies, and the frequency content is densest around the frequency of the VT/VF.

In addition, even in the presence of a substantial amount of noise, a PSD of normal sinus rhythm differs from a PSD of VT/VF arrhythmia. Noise within the ECG signal may be characterized as entropy (i.e., randomness). Accordingly, various entropy calculations may be performed on a PSD to differentiate between a normal sinus rhythm signal with noise and a VT/VF signal. For example, an in-band entropy may be calculated for a PSD of an ECG signal as described in U.S. Pat. No. 9,724,008 entitled "System and Method for Distinguishing a Cardiac Event from Noise in an Electrocardiogram (ECG) Signal," the contents of which are incorporated by reference in their entirety herein. The first-band entropy may be calculated by converting the PSD to a probability distribution function (PDF) and calculating the entropy of the signal between 0 Hz and 2 Hz. Based on feature selection experimentation and physiological reasoning, the noise detection function may select features of the PSD (e.g., a dominant frequency of the PSD; in-band entropy of the PSD between frequencies of 2 Hz and 6 Hz; first-band entropy of the PSD between frequencies of 0 Hz and 2 Hz; and a variance of the PSD, which is extracted as described below) to extract from the PSD and submit to a machine learning classifier.

When a normal sinus rhythm (NSR) in the absence of noise is compared to an NSR contaminated with motion artifact or machine noise, some characteristics of the PSD remain the same. For example, because entropy is a measure of randomness, the entropy in the 0-2 Hz range of the PSD is similar for an NSR with and without noise. However, the PSD for an NSR without the presence of noise typically has much less information content in the 2-6 Hz range than a PSD for an NSR with a noisy signal. Variance can be selected as a feature that would be extracted from the PSD and submitted to the machine learning classifier because the variance of a distribution provides a "feel" for the relative spread of the distribution. If a PSD has most of the energy in the 0-2 Hz band and very little energy in the 2-6 Hz band, the variance is relatively small. However, a PSD with much energy in the 2-6 Hz band would provide a much wider variance of the PSD. A PSD for an NSR has most of the energy in the 0-2 Hz band, and a PSD for a VT/VF arrhythmia has more energy in the 2-6 Hz band. In order to calculate variance, it can be assumed that the PSD is a normal distribution, and the variance of the PSD is calculated by treating the PSD as a PDF and calculating the second moment.

With regard to the machine learning classifier, as described for example in U.S. Pat. No. 9,724,008, the machine learning classifier may be trained on data sets including noisy normal sinus rhythm signals (e.g., false positive detections) and tachyarrhythmia signals. For example, two classifiers for each detection channel (e.g., side-to-side channel and front-to-back channel) can be used, where each classifier produces a numerical value in a range from 0 to 1. For example, a 20-second buffer of an ECG signal is passed from a shared memory to be analyzed. An ECG score is compiled based on the outputs from the evaluation of each second of analysis as a master score covering the 20 seconds of ECG signal. Fewer or additional ECG signal can be used in evaluating the ECG score (e.g., the analysis can span a few seconds to multiple minutes, hours, or even days).

While operating in the default operating mode, for example, the ME detector 324 may select a threshold score for the noise classification. That is, if the score is above the threshold score, then the noise detection function confirms the cardiac condition and the medical device controller 120 may initiate the treatment sequence. However, if the score is less than the threshold score, then the event can be classified as noise and the treatment sequence can be held off while a new score is created based on continued monitoring.

In an implementation, the ME detector 324 may adjust the sensitivity of the noise detection function. For example, the threshold ECG score may be preset by a user through a user configuration screen (e.g., during an initial fitting and/or baselining process). As another example, the ME detector 324 may automatically determine the threshold ECG score. The sensitivity of the noise detection function may be decreased (e.g., and a specificity can be increased) to reduce a number of false positives due to patient vibration and/or vehicular vibration and/or motion. For example, adjustments may be made dynamically or automatically in relation to the level or intensity of the vibration and/or motion. In some examples, the threshold ECG score can be increased (e.g., to 12, 15 or more) depending on various sensor inputs. For example, the as a temperature sensor 20i in the vehicle 10 and/or a temperature sensor included in the medical device contextual sensors 321 senses changes in temperature within the passenger compartment of the vehicle, the threshold ECG score may be automatically raised according to a predetermined relationship with the temperature. Similarly, as a motion sensor associated with the wearable medical device 100 senses increased or decreased patient physical activity and/or movement, the threshold ECG score may be automatically raised or decreased according to a predetermined relationship with the level of detected activity or movement.

In some implementations, the cardiac signal can undergo one or more preprocessing and/or noise detection steps (e.g., based on a machine learning classifier algorithm), and in some implementations, the ECG score may be processed or converted into a different form before it is compared to the threshold. If the ECG score meets or exceeds the threshold, the ME detector 324 may determine that the patient may be experiencing a cardiac condition.

Medical Device Learning

In some implementations, the medical device controller 120 is configured to acquire data related to a pattern of use of the associated wearable medical device 100, including locations visited (e.g., based on data acquired by the location module 385), conditions experienced, treatments applied, and situations encountered, among others. The medical device controller 120 can use such pattern of use data to learn how the wearable medical device 100 has been used in the past, and to assist in determining settings for future uses. In some implementations, the pattern of use data can assist in selecting and/or transitioning to the vehicle operating mode and selecting and/or performing a treatment sequence. The data related to the pattern of use may be acquired automatically (e.g., during the first day or week of use by the patient) or manually (e.g., in response to input received by the user).

In some implementations, the medical device controller 120 can identify patterns of use unrelated to the location of the device to assist in operating mode selection. For example, the medical device controller 120 may identify that it typically enters the vehicle operating mode on weekdays at 7:00 AM. If a correlation between the operating mode and such patterns is sufficiently established, the medical device controller may automatically enter the vehicle operating mode at times that fit within the established pattern. In some implementations, rather than automatically entering the particular operating mode, the wearable medical device may "expect" to enter the vehicle operating mode, and thus may relax threshold conditions for entering the vehicle operating mode during particular time periods.

Pattern of use data can also be used to assist in selecting and/or performing a treatment sequence. The medical device controller 120 is configured to compare patient information to detection parameters to determine whether the patient is experiencing a cardiac condition, select a treatment sequence based on the experienced cardiac condition, and provide the treatment sequence. The patient can stop the treatment from being delivered by providing an input to the medical device controller 120. In some implementations, the medical device controller 120 can store information related to such overridden treatments to better refine the detection parameters. For example, if the patient always refuses a treatment that is suggested based on a particular detection parameter, a threshold related to that detection parameter may be heightened or lowered accordingly (e.g., to reduce the sensitivity of the wearable medical device with respect to the detection parameter).

The medical device controller 120 predicts and/or determines medical premonitory events and/or MEs based on one or more detection parameters (e.g., conditions), and such detection parameters may depend on the mode that the wearable medical device 100 is operating under at the time. One example of a detection parameter is related to the power spectral density (PSD) of a cardiac signal (e.g., an ECG signal). However, other detection parameters can be used instead of or in addition to the PSD. For example, one or more of the detection parameters can be related to other components of the patient's ECG signal, such as waveform shape variations (e.g., QRS shape), duration variations (e.g., QRS or T-wave width, ST segment width), amplitude variations (e.g., R wave or T-wave amplitude), period variations (e.g., R-R interval, QT interval, ST interval), T wave alternans (TWA), heart rate variability (HRV), heart rate turbulence (HRT), PR interval, slurring of the QRS complex, premature ventricular contraction (PVC), frequency analysis, a VT or VF template, QT variability, QT interval length, and/or combinations and/or ratios of the aforementioned.

In some implementations, the wearable medical device 100 is configured to interact with one or more other medical devices. While the wearable medical device 100 described herein has been described as including a variety of sensors, in some implementations, one or more of the sensors may instead be part of a separate medical device. For example, in some implementations, the wearable medical device 100 is configured to interact with a blood pressure monitor, a respiration monitor, a pulse oximeter, and/or a medical device that includes a photoplethysmograph (PPG) sensor. In some implementations, the wearable medical device 100 is configured to interact with a medical device that is configured to detect a heart rate condition in the patient. The medical device for detecting a heart rate condition can provide information to the wearable medical device 100, and the wearable medical device 100 can select a treatment sequence for correcting the particular heart rate condition (e.g., one or more pacing shocks).

The medical device may be configured to adjust one or more settings based on a predetermined relationship with one or more input signals from one or more sensors associated with the medical device. For example, such adjustments may be made dynamically and/or automatically in response to changing conditions. For example, the adjustments may occur within an open or closed loop system control scheme. Further, such adjustments may be made adaptively in response to learning patterns in the underlying changing conditions.

The predetermined relationship between the settings and input sensed signals may be based on any known or learned relationship between the underlying parameters, including single or multi-variable linear, non-linear (such as quadratic, logarithmic, exponential, etc.), and other kinds of relationships. In some cases, the predetermined relationship may be based on binary classifications, transformations of the underlying signals (e.g., discrete forms, frequency and/or other domains, etc.), and/or statistical analysis. In some examples, the relationship may be based on performing a multivariate regression analysis of the input sensed signals and deriving one or more equations to describe the relationship.

Additionally, one or more techniques may be employed to match, verify, and/or correlate information from one or more types of sensors against other types of sensors. For example, information from physiological sensors associated with the medical device may be compared to and/or correlated with information from physiological sensors in the vehicle.

The medical device may also be configured to analyze a plurality of input signals in order to adaptively effect changes to one or more settings. For example, the medical device may effect changes to the settings based on a series of decision nodes. Each node may be based on logic implemented to test one or more input signals (individually or in a predetermined combined format) from one or more sensors of the medical device against a threshold. An output of such decision nodes may cause one or more settings of the medical device to be increased, decreased, or otherwise adjusted.

In some implementations, machine learning classification or regression tools may be trained and validated on training/validation populations of sensed values corresponding to signals from the one or more sensors. Such machine learning based systems can be implemented in accordance with the principles described herein such that the medical device can adaptively change its operating mode based on the operating environment of the device.

For example, in some implementations, a machine learning based classifier model (e.g., a random forest classifier model) may be trained and validated on metrics relating to patient response button use (or other response mechanism) and corresponding ECG signals of the patient during periods when the patient response buttons are used. Such a model can assess times at which the patient pushes the response buttons and the corresponding ECG signals to determine if the patient is conscious or undergoing a treatable condition. Once trained, the model can be adaptively validated and its corresponding thresholds can be adjusted over time for assessing new input response button uses and corresponding ECG signals. In this way, the device can use machine learning to adaptively learn whether a treatable condition is likely when the device detects that the patient has pushed the response buttons based on prior historical data about the individual patient or a population of patients.

Any of the above techniques can be used alone or in combination in order to establish a relationship between the operating mode of the medical device and the sensed signals. In some situations, such techniques may be implemented within the one or more special operating modes as described herein.

Example Infrastructure

Various illustrative modules and/or components described in connection with the disclosure herein (e.g., the medical device controller 120, the memory 304, the medical device contextual sensors 321, the contextual sensor interface 322, the ME detector 324, the ME risk estimator 325, the operating condition analyzer 320, the patient sensor interface 312, the therapy delivery interface 302, the location module 385, the network interface 306, the vehicle sensor monitor 40, the occupant identification system 45, the autonomous driving controller 50, and subsystems 51, 52, 53, 54, 55, 56, 57, 58, and 59) may be implemented as electronic hardware, computer software, or combinations of both. To clearly illustrate this interchangeability of hardware and software, various illustrative modules and/or components, have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. The various illustrative modules and/or components described in connection with the disclosure herein may be implemented as or performed with a processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. The processor may be a microprocessor, controller, microcontroller, or state machine. The processor may also be implemented as a combination of computing devices, e.g., a combination of DSP and a microprocessor, a plurality of microprocessors, one or more microprocessors in conjunction with a DSP core, or any other such configuration.

Software running on the medical device controller 120 can be realized by processor-executable instructions stored, for example, in the memory 304, that upon execution cause one or more processing devices to carry out the processes and functions described above, for example, selecting an operating mode, selecting a treatment sequence, and/or performing a treatment sequence, among others. The instructions can include, for example, interpreted instructions such as script instructions, or executable code, or other instructions stored in a computer readable medium.

A server (e.g., the remote server 326 as shown in FIG. 3) can be distributively implemented over a network, such as a server farm, or a set of widely distributed servers or can be implemented in a single virtual device that includes multiple distributed devices that operate in coordination with one another. For example, one of the devices can control the other devices, or the devices may operate under a set of coordinated rules or protocols, or the devices may be coordinated in another fashion. The coordinated operation of the multiple distributed devices presents the appearance of operating as a single device.

In some examples, the components of the medical device controller 120 may be contained within a single integrated circuit package. A system of this kind, in which both a processor (e.g., the processor 318) and one or more other components (e.g., the operating condition analyzer 320, the ME detector 324, etc.) are contained within a single integrated circuit package and/or fabricated as a single integrated circuit, is sometimes called a microcontroller. In some implementations, the integrated circuit package includes pins that correspond to input/output ports (e.g., that can be used to communicate signals to and from one or more of the input/output interface devices).

Although an example processing system has been described above, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as storing, maintaining, and displaying artifacts can be implemented as one or more computer program products, i.e., one or more modules of computer program instructions encoded on a tangible program carrier, for example a computer-readable medium (e.g., the memory 304), for execution by, or to control the operation of, a processing system. The computer readable medium can be a machine readable storage device, a machine readable storage substrate, a memory device, or a combination of one or more of them.

The term "system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them. In some implementations, operating systems can include a Windows based operating system, OSX, or other operating systems. For instance, in some examples, the processor may be configured to execute a real-time operating system (RTOS), such as RTLinux, or a non-real time operating system, such as BSD or GNU/Linux.

A computer program (also known as a program, software, software application, script, executable logic, or code) can be written in any form of programming language, including compiled or interpreted languages, or declarative or procedural languages, and can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM, DVD-ROM, and Blu-Ray disks. The processor and the memory can be supplemented by, or incorporated in, special purpose logic circuitry. Sometimes a server (e.g., the remote server 326 as shown in FIG. 3) is a general purpose computer, and sometimes it is a custom-tailored special purpose electronic device, and sometimes it is a combination of these things. Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network such as the connection between the remote server 326 and the network interface 306 shown in FIG. 3. Examples of communication networks include a local area network ("LAN") and a wide area network ("WAN"), e.g., the Internet.

Having described several aspects of at least one example of this disclosure, the examples of the methods and apparatuses discussed herein are not limited in application to the details of construction and the arrangement of components set forth in this description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples. Accordingly, the foregoing description and drawings are by way of example only Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

What is claimed is:

1. An ambulatory external cardiac treatment device comprising:
   one or more sensing electrodes disposed in a wearable garment and configured to sense cardiopulmonary signals of a patient;
   a network interface; and
   one or more processors configured to:
      receive signals from one or more vehicle occupancy sensors,
      detect usage of the ambulatory external cardiac treatment device in a vehicle based on the received signals from the one or more vehicle occupancy sensors,
      determine an event estimation of risk score for a particular time period from the sensed cardiopulmonary signals,
      determine whether the event estimation of risk score exceeds a risk score threshold for the particular time period,
      detect whether a medical event is occurring in the patient based on the sensed cardiopulmonary signals and whether a medical premonitory event is occurring in the patient based on the event estimation of risk score exceeding the risk score threshold for the particular time period,
      if the medical event is detected to be occurring in the patient, provide first driving control information to the vehicle, via the network interface, based at least in part on the detected usage of the ambulatory external cardiac treatment device in the vehicle and the detected medical event, and
      if the medical premonitory event is detected to be occurring in the patient, provide second driving control information to the vehicle, via the network interface, based at least in part on the detected usage of the ambulatory external cardiac treatment device in the vehicle and at least one of the detected medical premonitory event or the event estimation of risk score.

2. The ambulatory external cardiac treatment device of claim 1 wherein the first and the second driving control information provided to the vehicle comprises driving control messages and wherein the one or more processors are configured to provide the driving control messages to an autonomous driving controller via the network interface.

3. The ambulatory external cardiac treatment device of claim 2 wherein the driving control messages comprise one or more of steering, acceleration, or braking messages.

4. The ambulatory external cardiac treatment device of claim 2 wherein the driving control messages comprise autonomous driving control messages.

5. The ambulatory external cardiac treatment device of claim 1 wherein the first and the second driving control information comprises navigation instructions.

6. The ambulatory external cardiac treatment device of claim 5 wherein the navigation instructions of the first driving control information comprise a request to change a navigation destination based on the detected medical event and the navigation instructions of the second driving control information comprise a request to change the navigation destination based on the detected medical premonitory event.

7. The ambulatory external cardiac treatment device of claim 1 wherein the received signals from the one or more vehicle occupancy sensors are indicative of a patient position in the vehicle.

8. The ambulatory external cardiac treatment device of claim 7 wherein the first and the second driving control information provided to the vehicle are further based at least in part on the patient position in the vehicle.

9. The ambulatory external cardiac treatment device of claim 1, wherein the one or more processors are configured to provide, via the network interface, one or more of notifications or alarms to a vehicle user interface disposed in the vehicle.

10. The ambulatory external cardiac treatment device of claim 9 wherein the notifications comprise one or more of an instruction to transfer patient data to emergency medical services or an instruction for a vehicle communications unit to connect to an emergency medical services communication network.

11. The ambulatory external cardiac treatment device of claim 1 wherein the medical event and the medical premonitory event comprise a cardiac event.

12. The ambulatory external cardiac treatment device of claim 1 wherein the one or more vehicle occupancy sensors are disposed in the vehicle and wherein the one or more processors are communicatively coupled, via the network interface, to the one or more vehicle occupancy sensors that are disposed in the vehicle.

13. The ambulatory external cardiac treatment device of claim 1 wherein the one or more vehicle occupancy sensors are disposed on the ambulatory external cardiac treatment device and are configured to determine that the ambulatory external cardiac treatment device is in the vehicle.

14. The ambulatory external cardiac treatment device of claim 1 comprising therapy electrodes in communication with the one or more processors.

15. The ambulatory external cardiac treatment device of claim 14 wherein the one or more processors are configured to adjust one or more therapy delivery parameters based on the detected usage of the ambulatory external cardiac treatment device in the vehicle.

16. The ambulatory external cardiac treatment device of claim 15 wherein the one or more therapy delivery parameters comprise a time delay before delivery of a therapeutic shock.

17. The ambulatory external cardiac treatment device of claim 15 wherein the therapy electrodes are configured to deliver one or more of defibrillation current or pacing pulses.

18. The ambulatory external cardiac treatment device of claim 1 wherein the one or more processors are configured to determine a geo-location of the ambulatory external cardiac treatment device.

19. The ambulatory external cardiac treatment device of claim 18 wherein the one or more processors are configured to determine navigation instructions based at least in part on the geo-location of the ambulatory external cardiac treatment device.

20. The ambulatory external cardiac treatment device of claim 18 comprising a location module configured to send one or more signals indicative of the geo-location of the ambulatory external cardiac treatment device to the one or more processors wherein the one or more processors are configured to determine the geo-location of the ambulatory external cardiac treatment device based on the one or more signals from the location module.

21. The ambulatory external cardiac treatment device of claim 18 wherein the one or more processors are configured to receive geo-location information from the vehicle and to determine the geo-location of the ambulatory external cardiac treatment device based on the geo-location information from the vehicle.

22. The ambulatory external cardiac treatment device of claim 1 comprising an audio interface configured to receive and provide audible information.

23. The ambulatory external cardiac treatment device of claim 1 wherein the cardiopulmonary signals of the patient comprise one or more of an electrocardiogram (ECG), a heart rate, or a blood pressure.

24. The ambulatory external cardiac treatment device of claim 1 wherein the particular time period is 1-60 minutes from the detection of the medical premonitory event.

25. The ambulatory external cardiac treatment device of claim 24 wherein the second driving control information comprises an instruction to pull the vehicle out of traffic.

26. The ambulatory external cardiac treatment device of claim 1 wherein the particular time period is one of 1-59 minutes from the detection of the medical premonitory event or 1-24 hours from the detection of the medical premonitory event.

27. The ambulatory external cardiac treatment device of claim 26 wherein the second driving control information comprises an instruction to alter at least a portion of a programmed trip itinerary.

* * * * *